(12) United States Patent
Schulte et al.

(10) Patent No.: US 8,283,319 B2
(45) Date of Patent: Oct. 9, 2012

(54) THERAPEUTIC APPLICATION OF KAZAL-TYPE SERINE PROTEASE INHIBITORS

(75) Inventors: Stefan Schulte, Marburg (DE); Ulrich Kronthaler, Deisenhofen (DE); Stefan Schmidbauer, Lahntal (DE); Thomas Weimer, Gladenbach (DE); Kay Hofmann, Cologne (DE)

(73) Assignee: CSL Behring GmbH, Marburg (DE)

( * ) Notice: Subject to any disclaimer, the term of this patent is extended or adjusted under 35 U.S.C. 154(b) by 35 days.

(21) Appl. No.: 12/526,758

(22) PCT Filed: Feb. 11, 2008

(86) PCT No.: PCT/EP2008/001009
§ 371 (c)(1),
(2), (4) Date: Aug. 11, 2009

(87) PCT Pub. No.: WO2008/098720
PCT Pub. Date: Aug. 21, 2008

(65) Prior Publication Data
US 2010/0279923 A1    Nov. 4, 2010

(30) Foreign Application Priority Data

Feb. 12, 2007 (EP) .................................. 07002903

(51) Int. Cl.
*A61K 38/16* (2006.01)
*C07K 14/00* (2006.01)

(52) U.S. Cl. ............... 514/13.7; 514/14.2; 514/14.9; 514/21.3; 530/324; 530/345; 530/409

(58) Field of Classification Search .................. None
See application file for complete search history.

(56) References Cited

U.S. PATENT DOCUMENTS

| 5,126,322 A | 6/1992 | Collins et al. |
|---|---|---|
| 6,403,077 B1 | 6/2002 | Strom et al. |
| 2004/0087778 A1 | 5/2004 | Feige et al. |
| 2006/0127389 A1* | 6/2006 | Shi et al. ............ 424/94.64 |
| 2007/0178448 A1* | 8/2007 | Tsao et al. .............. 435/5 |

FOREIGN PATENT DOCUMENTS

DE     19848785 A1 *  4/2000
(Continued)

OTHER PUBLICATIONS

Machine translation of DE 19848785 (Apr. 27, 2000).*

(Continued)

*Primary Examiner* — Jeffrey E Russel
(74) *Attorney, Agent, or Firm* — Finnegan, Henderson, Farabow, Garrett & Dunner, L.L.P.

(57) ABSTRACT

The present invention relates to the therapeutic application of the Kazal-type serine protease inhibitor Infestin or domains thereof or modified Kazal-type serine protease inhibitors based on Infestin homologs, which prevent the formation and/or stabilization of three-dimensional arterial or venous thrombi by interfering with proteins involved in activation of the so-called intrinsic coagulation pathway. The present invention also relates to the use of Kazal-type serine protease inhibitors or fragments thereof or modified Kazal-type serine protease inhibitors in the treatment or prophylaxis of a condition or disorder related to arterial thrombus formation, i.e. stroke or myocardial infarction, inflammation, complement activation, fibrinolysis, angiogenesis and/or diseases linked to pathological kinin formation such as hypotonic shock, edema including hereditary angioedema, bacterial infections, arthritis, pancreatitis, or articular gout, Disseminated Intravasal Coagulation (DIC) and sepsis.

17 Claims, 13 Drawing Sheets

Figure 1:
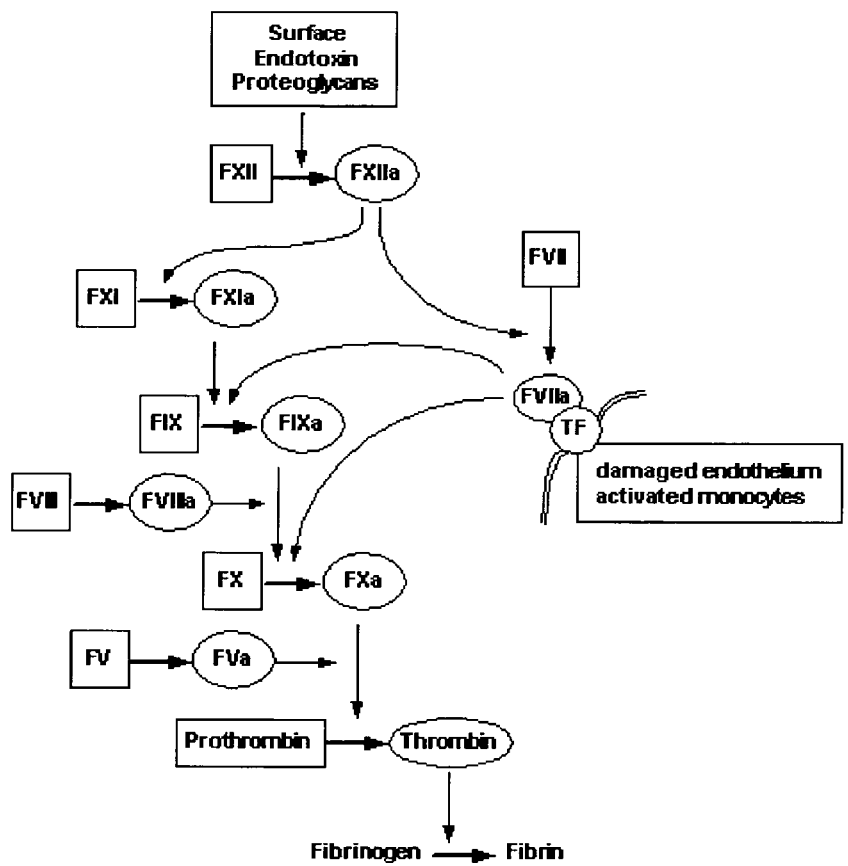

Inhibition of FXII following application of 100 and 200 mg/kg rHA-Infestin-4 (i.v.) in mice (prior to administration and) up to 4.5 hours

FOREIGN PATENT DOCUMENTS

| | | | |
|---|---|---|---|
| EP | 0278112 | A2 | 12/1987 |
| EP | 0258067 | A2 | 3/1988 |
| EP | 0258067 | A3 | 3/1988 |
| EP | 0352089 | A2 | 1/1990 |
| WO | WO 88/03171 | | 5/1988 |
| WO | WO 01/79271 | A1 | 10/2001 |
| WO | WO 03/076567 | A2 | 9/2003 |
| WO | WO 03/076567 | A3 | 9/2003 |
| WO | WO 2004/101740 | A2 | 11/2004 |
| WO | WO 2004/101740 | A3 | 11/2004 |
| WO | WO 2005/000892 | A2 | 1/2005 |
| WO | WO 2005/001025 | A2 | 1/2005 |
| WO | WO 2005/001025 | A3 | 1/2005 |
| WO | WO 2005/024044 | A2 | 3/2005 |
| WO | WO 2005/024044 | A3 | 3/2005 |
| WO | WO 2005/063808 | A1 | 7/2005 |
| WO | WO 2006/000448 | A2 | 1/2006 |
| WO | WO 2006/000448 | A3 | 1/2006 |
| WO | WO 2006/066878 | A1 | 6/2006 |

OTHER PUBLICATIONS

Beattie W.G. and Dugaiczyk A., "Structure and evolution of human α-fetoprotein deduced from partial sequence of cloned cDNA," *Gene*, 20:415-22 (1982).

Bettini R. et al., Review of "Handbook of pharmaceutical excipients, 3$^{rd}$ Ed." by Kibbe A. (ed.), *J. Control. Release*, 71:352-53 (2001).

Campos I.T.N. et al., "Infestin, a thrombin inhibitor presents in *Triatoma infestans* midgut, a Chagas' disease vector: gene cloning, expression and characterization of the inhibitor," *Insect Biochem. Mol. Biol.*, 32:991-97 (2002).

Campos I.T.N. et al., "Identification and characterization of a novel factor XIIa inhibitor in the hematophagous insect, *Triatoma infestans* (Hemiptera: Reduviidae)," *FEBS Lett.*, 577:512-16 (2004).

Chrenek P. et al., "Expression of recombinant human factor VIII in milk of several generations of transgenic rabbits," *Transgenic Res.*, 16:353-61 (2007).

Coleman R.W., "Contact activation pathway: Inflammatory, fibrinolytic, anticoagulant, antiadhesive, and antiangiogenic activities," in *Hemostasis and thrombosis: Basic principles and clinical practice, 4$^{th}$ ed.*, Chapter 6 (Coleman R.W. et al. eds., Lippincott Williams & Wilkins, Philadelphia, PA, 2001).

Coleman R.W., "Are hemostasis and thrombosis two sides of the same coin?" *J. Exp. Med.*, 203:493-95 (2006).

Cooke N.E. and David E.V., "Serum vitamin D-binding protein is a third member of the albumin and alpha fetoprotein gene family," *J. Clin. Invest.*, 76:2420-24 (1985).

Girolami A. et al., "The occasional venous thromboses seen in patients with severe (homozygous) FXII deficiency are probably due to associated risk factors: a study of prevalence in 21 patients and review of the literature," *J. Thromb. Thrombolysis*, 17:139-43 (2004).

Halbmayer W.M. et al., "Factor XII (Hageman factor) deficiency: a risk factor for development of thromboembolism. Incidence of FXII deficiency in patients after recurrent venous or arterial thromboembolism and myocardial infarction," *Wien. Med. Wochenschr.*, 143:43-50 (1993).

Hoffman C.S. and Winston F., "Isolation and characterization of mutants constitutive for expression of the *fbp1* gene of *Schizosaccharomyces pombe*," *Genetics*, 124:807-16 (1990).

Isawa H. et al., "A mosquito salivary protein inhibits activation of the plasma contact system by binding to factor XII and high molecular weight kininogen," *J. Biol. Chem.*, 277:27651-58 (2002).

Kleinschnitz C. et al., "Targeting coagulation factor XII provides protection from pathological thrombosis in cerebral ischemia without interfering with hemostasis," *J. Exp. Med.*, 203:513-18 (2006).

Koster T. et al., "John Hageman's factor and deep-vein thrombosis: Leiden thrombophilia study," *Br. J. Haematol.*, 87:422-24 (1994).

Kuhli C. et al., "Factor XII deficiency: a thrombophilic risk factor for retinal vein occlusion," *Am. J. Ophthalmol.*, 137:459-64 (2004).

Laskowski M. and Kato I., "Protein inhibitors of proteinases," *Ann. Rev. Biochem.*, 49:593-626 (1980).

Lazaris A. et al., "Transgenesis using nuclear transfer in goats," in *Methods in molecular biology*, vol. 348, Chapter 14 (Verma P.J. and Trounson A. eds., Humana Press Inc., Totowa, NJ, 2006).

Lee G., Review of "Pharmaceutical formulation development of peptides and proteins" by S. Frokjaer et al., *Euro. J. Pharm. and Biopharm.*, 50:329 (2000).

Lichenstein H.S., "Afamin is a new member of the albumin, α-fetoprotein, and vitamin D-binding protein gene family," *J. Biol. Chem.*, 269:18149-54 (1994).

Ma J.K.C. et al., "The production of recombinant pharmaceutical proteins in plants," *Nat. Rev. Genet.*, 4:794-805 (2003).

Mackman N., "Role of tissue factor in hemostasis, thrombosis, and vascular development," *Arterioscler. Thromb. Vasc. Biol.*, 24:1015-22 (2004).

Maundrell K., "*nmt1* of fission yeast," *J. Biol. Chem.*, 265:10857-64 (1990).

Pollock D.P. et al., "Transgenic milk as a method for the production of recombinant antibodies," *J. Immunol. Methods*, 231:147-57 (1999).

Ratnoff O.D. and J.E. Colopy, "A familial hemorrhagic trait associated with a deficiency of a clot-promoting fraction of plasma," *J. Clin. Invest.*, 34:602-13 (1955).

Renee T. et al., "Defective thrombus formation in mice lacking coagulation factor XII," *J. Exp. Med.*, 202:271-81 (2005).

Search Report for EP 07002903.8 dated Aug. 30, 2007.

Warren B.L. et al., "High-dose antithrombin III in severe sepsis: A randomized controlled trial," *JAMA*, 286:1869-78 (2001).

Werle M. and Bernkop-Schnürch A., "Strategies to improve plasma half life time of peptide and protein drugs," *Amino Acids*, 30:351-67 (2006).

Williams A. and Baird L.G., "DX-88 and HAE: a developmental perspective," *Transfus. Apheresis. Sci.*, 29:255-58 (2003).

Zeerleder S. et al., "Reevaluation of the incidence of thromboembolic complications in congenital factor XII deficiency," *Thromb. Haemost.*, 82:1240-46 (1999).

\* cited by examiner

Model of pathogenic thrombosis as discussed by Colman (Colman RW. 2006. Are hemostasis and thrombosis two sides of the same coin? J. Exp. Med. 203:493-495).

Figure 2:

Amino acid sequence similarity between Infestin-4 (I4) and SPINK-1 (SP)

*, identical; |, similar amino acid

```
I4   EVRNPC-------ACPRNYVPVCGSDGKTYGNPCMLNCAANQTKVPGLRLVHEGRC    (SEQ ID NO.: 5)
     *  | |      * | *****|** **|* *|* *  |     *|    * |*
SP:  DSLGREAK----CYNELNGCTKIYDPVCGTDSNTYPNECVL-CFENRKRQTSILIQKSGPC (SEQ ID NO.: 1)
```

Figure 3:

Contact sites of *R. prolixus* inhibitor with thrombin are indicated by # and contact sites of SPINK-1 with chymotrypsin by +.

```
         ###      ########           # ##                # #
Rpro     EGGEPC--------ACPHALHRVCGSDGETYSRFCTLMCAKFNGRPELVKVHDGFC   (SEQ ID NO.: 26)
I4       EVRNPC--------ACFRNYVPVCGSDGKTYGNPCMLNCAAQTRVPGLKLVHEGRC   (SEQ ID NO.: 5)
SP       GREAKCYNELNGCTKIYDPVCGTDGNTYPNECVL--CFENRKRTSLLIQKSGPC   (SEQ ID NO.: 1)
              + +           +             +
```

Figure 4:

Amino acid sequences of Infestin-4 (I4), SPINK1 (SP) and three SPINK1 mutants (K1-K3); * denotes identical, | similar amino acids with regard to the Infestin-4 sequence. The underlines sequence of I4 was used to replace 15 amino acids of SPINK-1 to generate mutant K1. Mutants K2 and K3 were generated by additional point mutations (amino acids underlines) on the K1 sequence.

```
I4:        EVRNPC------ACFFRNYVPVCGSDGKTYGNPCMLNCAAQTKVPGLKLV--HEGRC   (SEQ ID NO.: 5)
SP: DSLGREAK--CYNELNGCTKIYDPVCGTKGNTYPNECVL--CFENRKRKQTSILIQKSGPC   (SEQ ID NO.: 1)
K1: DSLGREVRNPC------ACFFRNYVPVCGTDGNTYPNECVL--CFENRKRKQTSILIQKSGPC (SEQ ID NO.: 2)
    *******| ****** ***|**|***** |**********   ***************
K2: DSLGREVRNPC------ACFFRNYVPVCGTDGNTYGNECML--CAENREKQTSILIQKEGPC (SEQ ID NO.: 3)
    *******     ****** ******** |*|**** |**    **|** ********|***
K3: DSLGREVRNPC------ACFFRNYVPVCGTDGNTYGNECMLNCAENRKRKQTSILIQKEGPC (SEQ ID NO.: 4)
    *******     ****** ******** |*|****|****  **|** *********|***
```

Effect of rHA-Infestin-4 in vitro on aPTT and FXII activity in mouse plasma

Prolongation of aPTT following 100 and 200 mg/kg application of rHA-Infestin-4 (i.v.) in mice (prior to administration and) up to 4.5 hours Inhibition of FXII following application of 100 and 200 mg/kg rHA-Infestin-4 (i.v.) in mice (prior to administration and) up to 4.5 hours Time course of rHA-Infestin-4 in plasma following i.v. injection of 100 mg/kg (mean; n=1-2/time point)

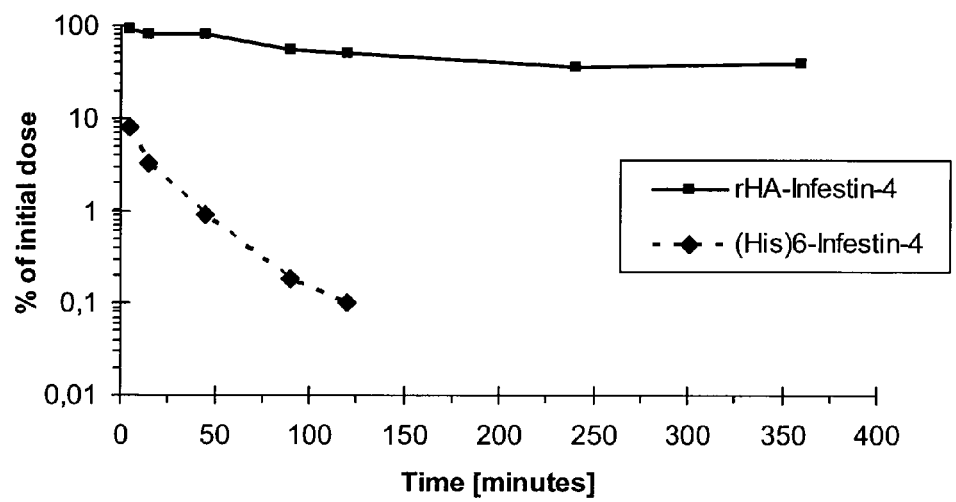
Figure 9: Comparison of pharmacokinetics of (His)6-Infestin and rHA-Infestin-4 in mice Figure 10: Effect of rHA-Infestin-4 on time to hemostasis (n=10-15/group, mean±SD)
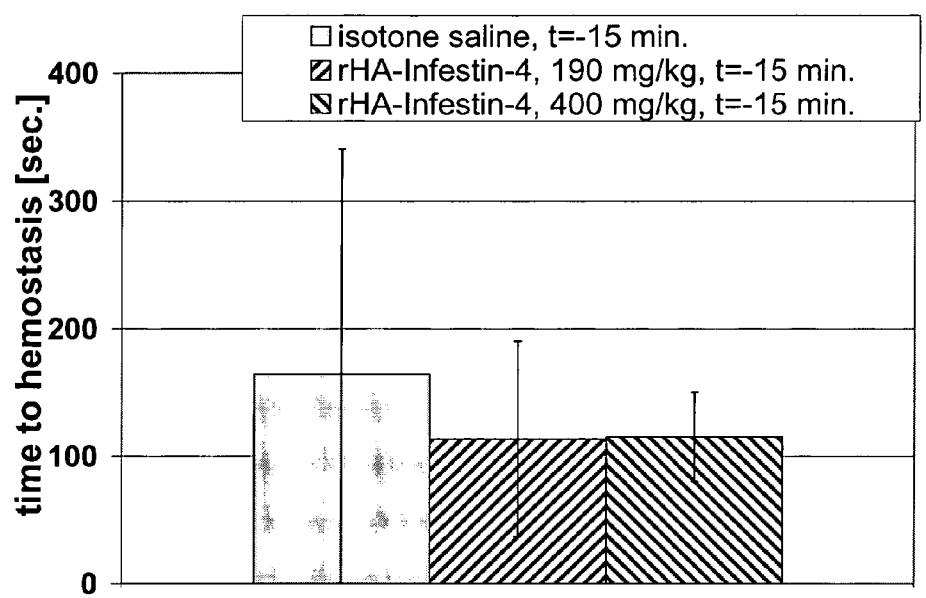

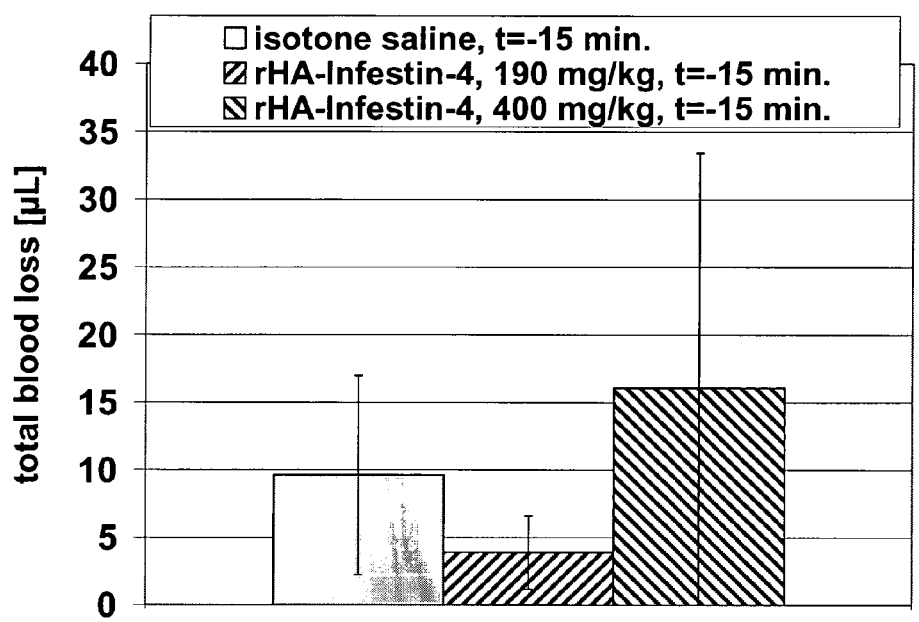
Figure 11: Effect of rHA-Infestin-4 on total blood loss (n=10-15/group, mean±SD)

Figure 12: Effect of rHA-Infestin-4 on time to hemostasis (n=10-15/group, individual data)
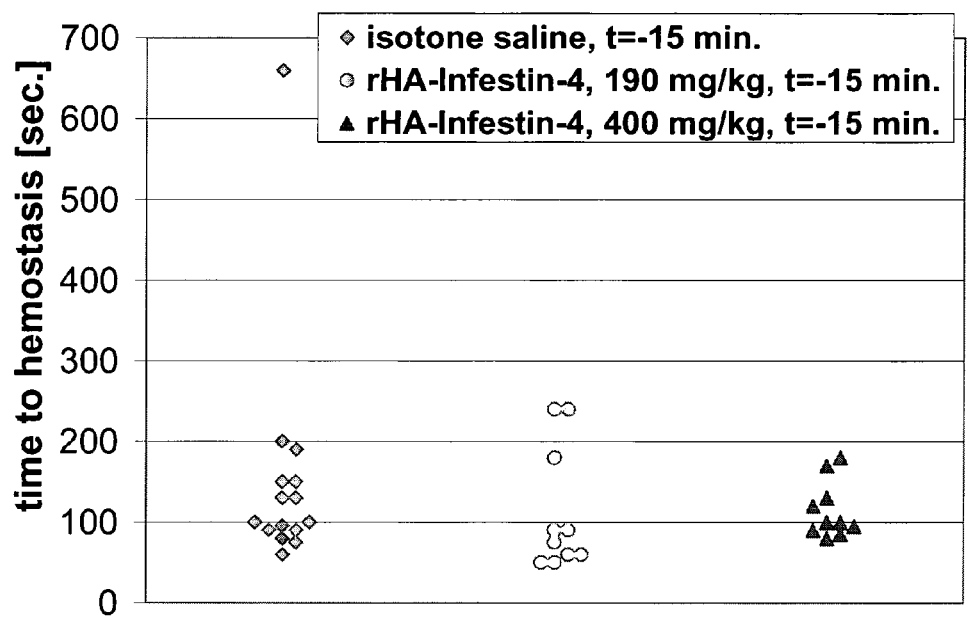

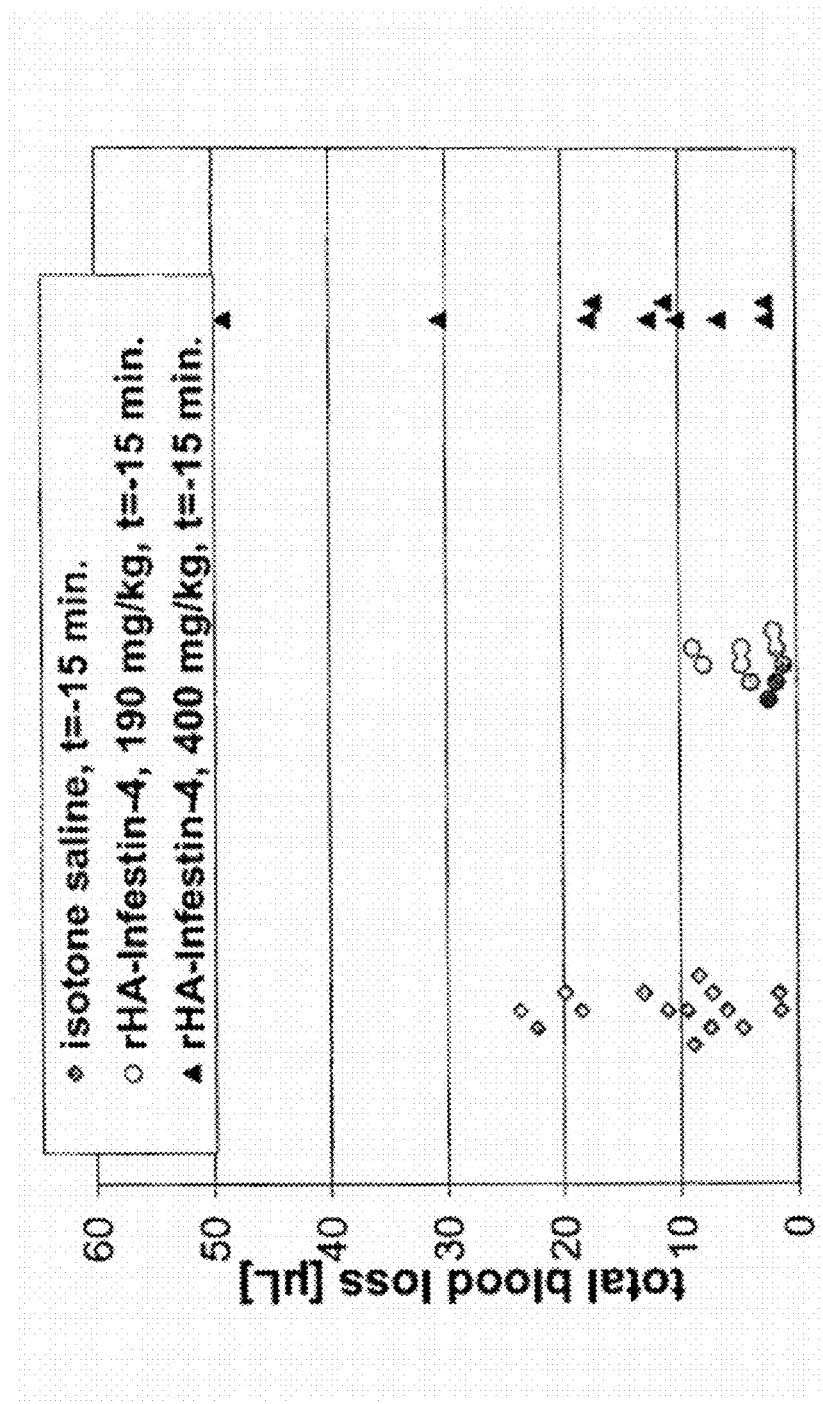
Figure 13: Effect of rHA-Infestin-4 on total blood loss (n=10-15/group, individual data)

THERAPEUTIC APPLICATION OF KAZAL-TYPE SERINE PROTEASE INHIBITORS

This is a national stage entry of PCT/EP2008/001009, filed Feb. 11, 2008, which claims priority to EP 07002903.8, filed Feb. 12, 2007, all of which are incorporated herein by reference.

The subject of the present invention is, in the most general aspect, the therapeutic application of the Kazal-type serine protease inhibitor Infestin or domains thereof or modified Kazal-type serine protease inhibitors based on Infestin homologs, which prevent the formation and/or stabilization of three-dimensional arterial or venous thrombi by interfering with proteins involved in activation of the so-called intrinsic coagulation pathway. In particular the present invention relates to the use of said Kazal-type serine protease inhibitors or fragments thereof or modified Kazal-type serine protease inhibitors, in the treatment or prophylaxis of a condition or disorder related to arterial thrombus formation, i. e. stroke or myocardial infarction, inflammation, complement activation, fibrinolysis, angiogenesis and/or diseases linked to pathological kinin formation such as hypotonic shock, edema including hereditary angioedema, bacterial infections, arthritis, pancreatitis, or articular gout, Disseminated Intravasal Coagulation (DIC) and sepsis.

Vessel wall injury triggers sudden adhesion and aggregation of blood platelets, followed by the activation of the plasma coagulation system and the formation of fibrin-containing thrombi, which occlude the site of injury. These events are crucial to limit post-traumatic blood loss but may also occlude diseased vessels leading to ischemia and infarction of vital organs. In the waterfall model, blood coagulation proceeds by a series of reactions involving the activation of zymogens by limited proteolysis culminating in generation of thrombin, which converts plasma fibrinogen to fibrin and activates platelets. In turn, collagen- or fibrin-adherent platelets facilitate thrombin generation by several orders of magnitude via exposing procoagulant phospholipids (mainly phosphatidyl serine) on their outer surface, which propagates assembly and activation of coagulation protease complexes and by direct interaction between platelet receptors and coagulation factors.

Two converging pathways for coagulation exist that are triggered by either extrinsic (vessel wall) or intrinsic (blood-borne) components of the vascular system. The "extrinsic" pathway is initiated by the complex of the plasma factor VII (FVII) with the integral membrane protein tissue factor (TF), an essential coagulation cofactor that is absent on the luminal surface but strongly expressed in subendothelial layers of the vessel and which is accessible or liberated via tissue injury. TF expressed in circulating microvesicles might also contribute to thrombus propagation by sustaining thrombin generation on the surface of activated platelets.

The "intrinsic" or contact activation pathway is initiated when factor XII (FXII, Hageman factor) comes into contact with negatively charged surfaces in a reaction involving high molecular weight kininogen and plasma kallikrein. FXII can be activated by macromolecular constituents of the subendothelial matrix such as glycosaminoglycans and collagens, sulfatides, nucleotides and other soluble polyanions or non-physiological material such as glass or polymers. One of the most potent contact activators is kaolin and this reaction serves as the mechanistic basis for the major clinical clotting test, the activated partial thromboplastin time (aPTT), which measures the coagulation capacity via the "intrinsic" pathway. In reactions propagated by platelets, activated FXII then activates FXI to FXIa and subsequently FXIa activates factor IX. The complex of FVIIIa, which FVIIIa has been previously activated by traces of FXa and/or Thrombin, and FIXa (the tenase complex) subsequently activates FX (see FIG. 1, "left arm"). Despite its high potency to induce blood clotting in vitro, the (patho) physiological significance of the FXII-triggered intrinsic coagulation pathway is questioned by the fact that hereditary deficiencies of FXII as well as of high molecular weight kininogen and plasma kallikrein are not associated with bleeding complications. Together with the observation that humans and mice lacking extrinsic pathway constituents such as TF and FVII suffer from severe bleeding this has led to the current hypothesis that for the cessation of bleeding in vivo exclusively the extrinsic cascade is required (Mackman, N. 2004. Role of tissue factor in hemostasis, thrombosis, and vascular development. Arterioscler. Thromb. Vasc. Biol. 24, 1015-1022).

In pathological conditions, the coagulation cascade may be activated inappropriately which then results in the formation of haemostatic plugs inside the blood vessels. Thereby, vessels can be occluded and the blood supply to distal organs limited. This process is known as thromboembolism and is associated with high mortality. In addition, the use of prosthetic devices, which come into contact with blood, is severely limited because of activation of the intrinsic coagulation cascade. Suitable coating of the prosthetic surface may avoid said problem in some cases but may compromise its function in others. Examples of such prosthetic devices are haemodialysers, cardiopulmonary by-pass circuits, heart valves, vascular stents and in-dwelling catheters. In cases where such devices are used, anticoagulants, such as heparin, are administered to prevent fibrin formation on the surface. However, some patients are intolerant of heparin, which can cause heparin-induced thrombocytopenia (HIT) resulting in platelet aggregation and life-threatening thrombosis. Furthermore, an inherent disadvantage of all anticoagulants used in clinics is an increased risk of serious bleeding events. Therefore, a strong need for new types of anticoagulants exist, which are not associated with such complications and that can be used in affected patients or as superior therapy concept preventing thrombosis without increased bleeding risks (Renne T et al. 2005. Defective thrombus formation in mice lacking factor XII. J. Exp. Med. 202:271-281).

In WO2006/066878 the use of antibodies against FXII/FXIIa or the use of inhibitors of FXII/FXIIa is proposed. As potential inhibitors antithrombin III (AT III), angiotensin converting enzyme inhibitor, C1 inhibitor, aprotinin, alpha-1 protease inhibitor, antipain ([(S)-1-Carboxy-2-Phenylethyl]-Carbamoyl-L-Arg-L-Val-Arginal), Z-Pro-Pro-aldehyde-dimethyl acetate, DX88 (Dyax Inc., 300 Technology Square, Cambridge, Mass. 02139, USA; cited in: Williams A and Baird L G. 2003. DX-88 and HAE: a developmental perspective. Transfus Apheresis Sci. 29:255-258), leupeptin, inhibitors of prolyl oligopeptidase such as Fmoc-Ala-Pyr-CN, corn-trypsin inhibitor, mutants of the bovine pancreatic trypsin inhibitor, ecotin, yellowfin sole anticoagulant protein, Cucurbita maxima trypsin inhibitor-V including Curcurbita maxima isoinhibitors and Hamadarin (as disclosed by Isawa H et al. 2002. A mosquito salivary protein inhibits activation of the plasma contact system by binding to factor XII and high molecular weight kininogen. J. Biol. Chem. 277:27651-27658) have been proposed.

An ideal inhibitor of FXII/FXIIa as a therapeutic agent—while exhibiting a high inhibitory activity towards FXII/FXIIa—will not increase the risk of bleeding, be non-immunogenic and have to be administered as sparingly as possible ideally only once. Small molecule inhibitors like Z-Pro-Proaldehyde-dimethyl acetate will have only a very short half-life after administration requiring multiple injections or would have to be developed into orally available slow release forms and then also be given constantly over a long period. Human plasma proteins like C1 inhibitor would at first sight fulfill all requirements, having a relatively high inhibitory activity towards FXII/FXIIa while not increasing the risk of bleeding, being non-immunogenic as a human protein and also having a considerably long plasma half-life.

It was now surprisingly found that in an in vivo model of thrombogenicity C1 inhibitor as a prime candidate of a human FXII/FXIIa inhibitor could not be used successfully to prevent occlusion. Another proposed FXII/FXIIa inhibitor from human plasma namely AT III inhibitor would at least not fulfill the second requirement as the bleeding risk would increase using it as an inhibitor of FXII/FXIIa (Warren B L et al. 2001. Caring for the critically ill patient. High-dose antithrombin III in severe sepsis: a randomized controlled trial. JAMA 286:1869-1878).

Hence, it is apparent that there still exists a need for an improved medication for the treatment and/or prophylaxis of thrombosis and similar disorders. Therefore, it is an object of the present invention to satisfy such a need.

For more than five decades it has been known that deficiency of coagulation factor XII is not associated with increased spontaneous or injury related bleeding complications (Ratnoff O D & Colopy J E 1955. A familial hemorrhagic trait associated with a deficiency of a clot-promoting fraction of plasma. J Clin Invest 34:602-613). Indeed, although readily detected by a pathological value measured in the aPTT (a clinical clotting test that addresses the intrinsic pathway of coagulation) humans that are deficient in FXII do not suffer from abnormal bleeding even during major surgical procedures (Colman R W. Hemostasis and Thrombosis. Basic principles & clinical practice (eds. Colman R W, Hirsch J, Mader V J, Clowes A W, & George J) 103-122 (Lippincott Williams & Wilkins, Philadelphia, 2001)). In contrast, deficiency of FXII had been associated with increased risk of venous thrombosis (Kuhli C et al. 2004. Factor XII deficiency: a thrombophilic risk factor for retinal vein occlusion. Am. J. Ophthalmol. 137:459-464; Halbmayer W M et al. 1993. Factor XII (Hageman factor) deficiency: a risk factor for development of thromboembolism. Incidence of FXII deficiency in patients after recurrent venous or arterial thromboembolism and myocardial infarction. Wien. Med. Wochenschr. 143:43-50). Studies and case reports supporting this idea refer to the index case for FXII deficiency, Mr. John Hageman, who died of pulmonary embolism. The hypothesis that FXII deficiency is associated with an increased prothrombotic risk is challenged by a recent reevaluation of several case reports the original reports of which linked FXII deficiency with thrombosis (Girolami A et al. 2004. The occasional venous thromboses seen in patients with severe (homozygous) FXII deficiency are probably due to associated risk factors: A study of prevalence in 21 patients and review of the literature. J. Thromb. Thrombolysis 17:139-143). In most cases the authors identified concomitant congenital or acquired prothrombotic risk factors in combination with factor FXII deficiency that could be responsible for the thrombotic event independently of FXII. The largest epidemiological studies using well characterized patients (Koster T et al. 1994. John Hageman's factor and deep-vein thrombosis: Leiden thrombophilia Study. Br. J. Haematol. 87:422-424) and FXII-deficient families (Zeerleder S et al. 1999. Reevaluation of the incidence of thromboembolic complications in congenital factor XII deficiency—a study on 73 subjects from 14 Swiss families. Thromb. Haemost. 82:1240-1246) indicated that there is no correlation of FXII deficiency and any pro- or anti-thrombotic risk.

Surprisingly and in contrast to common believe of those skilled in the art it has been discovered that the factor XII-driven intrinsic coagulation pathway is involved in arterial thrombus formation in vivo but is not necessary for normal tissue-specific hemostasis (Kleinschnitz C et al. 2006. Targeting coagulation factor XII provides protection from pathological thrombosis in cerebral ischemia without interfering with hemostasis. J. Exp. Med. 203:513-518; WO 2006/066878). Unexpectedly, these results place factor XII in a central position in the process of pathological thrombus formation (FIG. 1). Hence substances capable of interfering and blocking FXII activation or FXIIa activity may be suited to block pathogenic arterial thrombus formation and the clinical consequences thereof.

Recently a novel inhibitor of FXII/FXIIa was discovered in insects: Infestin domains 3-4 (Infestin 3-4) and Infestin domain 4 (Infestin-4) from the midgut of *Triatoma infestans*, a hematophagous insect (Campos ITN et al. 2002. Infestin, a thrombin inhibitor present in *Triatoma infestans* midgut, a Chagas' disease vector: gene cloning, expression and characterization of the inhibitor. Insect Biochem. Mol. Biol. 32:991-997; Campos ITN et al. 2004. Identification and characterization of a novel factor XIIa inhibitor in the hematophagous insect, *Triatoma infestans* (Hemiptera: Reduviidae). FEBS Lett. 577:512-516). These proteins are known as potent FXIIa inhibitors of the Kazal-type serine protease inhibitors, prolonging activated partial thromboplastin time approximately by factor 3.

These inhibitors have not been evaluated in terms of therapeutic application for blocking pathogenic thrombus formation. In addition, it has also not been tried to reduce the immunogenicity of these heterologous inhibitors in humans and to extend their in-vivo half-lives.

It was surprisingly found that the Kazal-type serine protease inhibitor domain Infestin-4 protected mice against pathogenic thrombus formation while no increased bleeding risk was observed in these animals. To increase plasma half-life Infestin-4 was expressed as a fusion to human albumin in mammalian cells and purified from cell culture supernatant. The purified inhibitor was injected into mice and a thrombotic challenge was induced with the aid of $FeCl_3$. 100% of the mice treated with rHA-Infestin-4 were protected whereas in the vast majority of the untreated control mice vessel occlusion occurred. The lack of associated bleeding risk is demonstrated by tail clipping experiments. Infestin-4 treated as well as untreated control mice display comparable time to hemostasis and blood loss. Thus, in-vivo protection against thrombosis in combination with a negligible bleeding risk is demonstrated for recombinant Infestin-4 in mice. Infestin 3-4 in this respect is comprised under the term of Infestin-4 but the preferred compound is Infestin-4 or mixtures of both Infestin 3-4 with predominantly Infestin-4.

rHA-Infestin-4 was also tested in vitro for its potential to specifically inhibit the intrinsic pathway by measuring the activated partial thromboplastin time (aPTT), which, in line with a substance effectively inhibiting the intrinsic pathway, was indeed prolonged. In contrast, the prothrombin time (PT), a test for factor VIIa/tissue factor-initiated activation of the extrinsic pathway of coagulation, was nearly unaffected. The reduction of FXII activity was also directly demonstrated on the basis of FXII deficient human plasma. Accordingly, the subject of the invention is the use of the Kazal-type serine protease inhibitor Infestin or fragments thereof, preferentially domain 3-4, most preferred domain 4, or fragments thereof as a medicament, more specifically for the manufacture of a medicament against thrombotic diseases prolonging the aPTT (leaving the PT essentially unaffected) and thereby preventing the formation and/or the stabilization of three-dimensional arterial or venous thrombi without concomitant bleeding risk. The respective inhibitor may hereby function to inhibit the intrinsic coagulation pathway, especially the activity of FXIIa, to inhibit formation and/or stabilization of three-dimensional arterial or venous thrombi.

Therefore, the present invention further provides a substance respective pharmaceutical for the treatment or prophylaxis of a condition or disorder related to arterial thrombus formation, i.e. stroke or myocardial infarction. Due to the multiple effector functions of FXIIa the substance respective pharmaceutical has additional therapeutic effect in complement activation, fibrinolysis, inflammation, angiogenesis and/or diseases linked to pathological kinin formation such as hypotonic shock, edema including hereditary angioedema, bacterial infections, arthritis, pancreatitis, or articular gout, Disseminated Intravasal Coagulation (DIC) and sepsis.

Modified Kazal-Type Serine Protease Inhibitors

The therapeutic administration of heterologous inhibitors like Infestin-4 in humans may generate an immune response. Therefore, another objective of this invention was to identify less immunogenic but still potent Kazal-type serine protease inhibitors. It was surprisingly found that by modifying one related human Kazal-type serine protease inhibitor (serine protease inhibitor Kazal-type 1, SPINK-1) in a way that the putative enzyme contact site(s) are replaced by the corresponding regions of Infestin-4, highly active FXIIa inhibitors were generated which can be used for the manufacture of substances especially for the treatment or prevention of thrombotic events. Based on these results it is possible to modify any natural Kazal-type serine protease inhibitor in a way that it becomes FXIIa specific. An example is described in the following section.

In order to generate a potent FXIIa inhibitor for therapeutic use in humans, we looked for a human protein with high similarity to Infestin-4, which should be less immunogenic in human patients than an insect derived protein. The human protein with highest similarity to Infestin-4 was found to be SPINK-1, Kazal-type serine protease inhibitor expressed in the pancreas (also known as pancreatic secretory trypsin inhibitor, PSTI). The similarities between Infestin-4 and SPINK-1 are out-lined in FIG. 2.

Based on the wild-type SPINK-1 sequence different mutants have been generated with increasing homology of the SPINK-1 sequence to Infestin-4. As no structural data were available for Infestin, data for a related inhibitor from *Rhodnius prolixus* in a complex with thrombin (PDB: 1TBQ) were analyzed. The *R. prolixus* inhibitor has two Kazal domains, the N-terminal of which interacts with the catalytic residues of thrombin. The N-terminal domain was therefore used as a basis for the comparison with Infestin-4. FIG. 3 shows the contact sites of the *R. prolixus* inhibitor with thrombin and the contact sites of SPINK-1 with chymotrypsin. A common feature of both Kazal-type serine protease inhibitors is the accumulation of contact sites in the N-terminal region. Assuming that this region transmits the specificity of the inhibition, several mutants of SPINK-1 were generated. For the first mutant, named K1, the presumed protease contact site in the amino-terminal part of SPINK-1 was replaced by that of Infestin-4. Further amino acid exchanges in mutants K2 and K3 were changing SPINK-1 closer towards the Infestin-4 sequence. FIG. 4 shows the amino acid sequence of these mutants and the degree of changes to the SPINK-1 wild-type sequence. The amino acid sequences of the mature SPINK-1 wild-type protein, the three mutants and Infestin-4 are given as SEQ ID NO 1 to 5. The term "SPINK-1 mutants with increasing respective increased homology" means mutants which have more than 20 identical amino acids with Infestin-4, or a conservative substitution instead of identity meaning a conservative substitution instead of an identical amino acid. These mutants are different from the mutants of the human pancreatic secretory trypsin inhibitor described in EP-A2-0352089, WO88/03171A and EP-A2-0278112.

SPINK-1 mutants were expressed and purified. The mutants were tested in vitro for their potential to specifically inhibit the intrinsic pathway by measuring the activated partial thromboplastin time (aPTT), which was prolonged as expected in the case of a substance capable of inhibiting the intrinsic pathway. In contrast, the Prothrombin time (PT), a test for factor VIIa/tissue factor-initiated activation of the extrinsic pathway of coagulation, was essentially unaffected.

Accordingly, another embodiment of the invention is the use of a modified form of the mammalian Kazal-type serine protease inhibitor SPINK-1, Infestin homologs or fragments thereof, or preferably Infestin domain 4 or fragments and homologs thereof, as a pharmaceutical, more specifically for the manufacture of a pharmaceutical against thrombotic diseases. The mode of action in these indications is the inhibition of FXII/FXIIa activity which can be measured by the aPTT which is prolonged (leaving the PT essentially unaffected). In this way, the formation and/or the stabilization of three-dimensional arterial or venous thrombi is prevented. The respective inhibitor may hereby function as an inhibitor of the intrinsic coagulation pathway, especially of the activity of FXIIa, so far as to inhibit formation and/or stabilization of three-dimensional arterial or venous thrombi.

Therefore, the present invention further provides substances with reduced risk of immunogenicity in humans for the treatment or prophylaxis of a condition or disorder related to arterial thrombus formation, i.e. stroke or myocardial infarction, complement activation, fibrinolysis, inflammation, angiogenesis and/or diseases linked to pathological kinin formation such as hypotonic shock, edema including hereditary angioedema, bacterial infections, cancer (Trousseau syndrome), arthritis, pancreatitis, or articular gout, Disseminated Intravasal Coagulation (DIC) or sepsis.

Other especially preferred proteins of the invention are human pancreas protease inhibitor SPINK-1 derived mutants as described above, wherein such mutants are characterized in that they have been changed to increase their homology with Infestin-4 protein with regard to the ability to inhibit the FXIIa activity. Such mutants are characterized in that they prolong activated partial thromboplastin time in vitro.

Infestin-4, Modified Mammalian Kazal-Type Serine Protease Inhibitors and Modified Kazal-Type Serine Protease Inhibitors with Extended Half-Lives Another aspect of the invention are Infestin-4 and modified mammalian Kazal-type serine protease inhibitors based on Infestin homologs or fragments thereof with extended half-life. As the Kazal-type serine protease inhibitors of the invention are rather small proteins, a rapid renal clearance as published for other small proteins can be expected (Werle M. and Bernkop-Schnurch A. 2006. Strategies to improve plasma half-life time of peptide and protein drugs. Amino Acids 30:351-367). One way to address a short plasma half-life of a polypeptidic compound is of course to inject it repeatedly or via continuous infusion. Preferably the intrinsic plasma half-life of the polypeptide itself is increased. It is therefore another aspect of the invention to provide Kazal-type serine protease inhibitors fused to half-life extending proteins (HLEP).

A "half-life enhancing polypeptide" (HLEP) as used herein is selected from the group consisting of albumin, a member of the albumin-family, the constant region of immunoglobulin G and fragments thereof and polypeptides capable of binding under physiological conditions to albumin, to members of the albumin family as well as to portions of an immunoglobulin constant region.

As specific examples of half-life enhancing polypeptides (HLEPs) albumin and immunoglobulins and their fragments or derivatives have been described.

Ballance et al. (WO 01/79271) described fusion polypeptides of a multitude of different therapeutic polypeptides which, when fused to human serum albumin, are predicted to have an increased functional half-life in vivo and extended shelf-life. The therapeutic protein may be fused directly or via a peptidic linker to the albumin moiety, and C- and N-terminal fusions are described.

The terms human serum albumin (HSA) and human albumin (HA) are used inter-changeably in this application. The terms "albumin" and "serum albumin" are broader, and encompass human serum albumin (and fragments and variants thereof) as well as albumin from other species (and fragments and variants thereof).

As used herein, "albumin" refers collectively to an albumin polypeptide or amino acid sequence, or an albumin fragment or variant, having one or more functional activities (e.g. biological activities) of albumin. In particular, "albumin" refers to human albumin or fragments thereof, especially the mature form of human albumin as shown in SEQ ID No:6 herein or albumin from other vertebrates or fragments thereof, or analogs or variants of these molecules or fragments thereof.

The albumin portion of the albumin fusion proteins may comprise the full length of the HA sequence as described above, or may include one or more fragments thereof that are capable of stabilizing or prolonging the therapeutic activity. Such fragments may be of 10 or more amino acids in length or may include about 15, 20, 25, 30, 50, or more contiguous amino acids from the HA sequence or may include part or all of specific domains of HA.

The albumin portion of the albumin fusion proteins of the invention may be a variant of normal HA. The therapeutic polypeptide portion of the fusion proteins of the invention may also be variants of the corresponding therapeutic polypeptides as described herein. The term "variants" includes insertions, deletions and substitutions, either conservative or non-conservative, where such changes do not substantially alter the active site, or active domain, which confers the therapeutic activities of the therapeutic polypeptides.

In particular, the albumin fusion proteins of the invention may include naturally occurring polymorphic variants of human albumin and fragments of human albumin. The albumin may be derived from any vertebrate, especially any mammal, for example human, monkey, cow, sheep, or pig. Non-mammalian albumins include, but are not limited to, such derived from hen and salmon. The albumin portion of the albumin-linked polypeptide may be from a different animal than the therapeutic polypeptide portion.

Generally speaking, an albumin fragment or variant will be at least 20, preferably at least 40, most preferably more than 70 amino acids long. The albumin variant may preferentially consist of or alternatively comprise at least one whole domain of albumin or fragments of said domains, for example domains 1 (amino acids 1-194 of SEQ ID NO 6), 2 (amino acids 195-387 of SEQ ID NO 6), 3 (amino acids 388-585 of SEQ ID NO 6), 1+2 (1-387 of SEQ ID NO 6), 2+3 (195-585 of SEQ NO 6) or 1+3 (amino acids 1-194 of SEQ ID NO 6+ amino acids 388-585 of SEQ ID NO 6). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

The albumin portion of an albumin fusion protein of the invention may comprise at least one subdomain or domain of HA or conservative modifications thereof. Besides albumin, alpha-fetoprotein, another member of the albumin family, has been claimed to extend the half-life of an attached therapeutic polypeptide in vivo (WO 2005/024044). The albumin family of proteins, evolutionarily related serum transport proteins, consists of albumin, alpha-fetoprotein (AFP; Beattie & Dugaiczyk 1982. Structure and evolution of human alpha-fetoprotein deduced from partial sequence of cloned cDNA. Gene 20:415-422), afamin (AFM; Lichenstein et al. 1994. Afamin is a new member of the albumin, alpha-fetoprotein, and vitamin D-binding protein gene family. J. Biol. Chem. 269: 18149-18154) and vitamin D binding protein (DBP; Cooke & David 1985. Serum vitamin D-binding protein is a third member of the albumin and alpha fetoprotein gene family. J. Clin. Invest. 76:2420-2424). Their genes represent a multigene cluster with structural and functional similarities mapping to the same chromosomal region in humans, mice and rat. The structural similarity of the albumin family members suggest their usability as HLEPs. It is therefore another object of the invention to use such albumin family members, fragments and variants thereof as HLEPs. The term "variants" includes insertions, deletions and substitutions, either conservative or non-conservative, where such changes do not substantially alter the active site, or active domain, which confers the therapeutic activities of the therapeutic polypeptides.

Albumin family members may comprise the full length of the respective protein AFP, AFM and DBP, or may include one or more fragments thereof that are capable of stabilizing or prolonging the therapeutic activity. Such fragments may be of 10 or more amino acids in length or may include about 15, 20, 25, 30, 50, or more contiguous amino acids of the respective protein sequence or may include part or all of specific domains of the respective protein.

Albumin family member fusion proteins of the invention may include naturally occurring polymorphic variants of AFP, AFM and DBP. The proteins may be derived from any vertebrate, especially any mammal, for example human, monkey, cow, sheep, or pig. Non-mammalian albumin family members include, but are not limited to, such derived from hen and salmon.

IgG and IgG-fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to extend the therapeutic proteins' in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly degraded in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life extending properties.

It is therefore another embodiment of the invention to use such immunoglobulin sequences, preferably Fc fragments and variants thereof as HLEPs. Kazal-type serine protease inhibitors like Infestin-4 and modified Kazal-type serine protease inhibitors with enhanced inhibitory specificity for FXIIa like the SPINK-1 mutants may be fused to Fc domains or at least portions of immunoglobulin constant regions as HLEPs and expressed in E. coli, yeast, insect, plant or vertebrate cells or in transgenic animals. A SPINK-K2-Fc fusion protein is exemplarily shown in SEQ ID No 25.

The invention specifically relates to fusion proteins, comprising linking a Kazal-type serine protease inhibitor like Infestin-4 and modified Kazal-type serine protease inhibitors like the SPINK-1 mutants or fragment or variant thereof to the N- or C-terminus of a HLEP or fragment or variant thereof such that the fusion protein formed has an increased in vivo half-life compared to the corresponding Kazal-type serine protease inhibitor which has not been linked to a HLEP. An intervening peptidic linker may be introduced between the therapeutic polypeptide and the HLEP. Should the HLEP interfere with the therapeutic polypeptide's specific activity e.g. by steric hindrance, cleavable linkers may be introduced. Preferred enzymes for linker cleavage are the coagulation proteases of the intrinsic coagulation pathway, FXIIa, FXIa, FIXa, FVIIIa or FXa, wherein the most preferred cleaving enzyme is FXIIa.

The Kazal-type serine protease inhibitor family is one of the numerous families of serine protease inhibitors. Many proteins from different species have been described (Laskowski M and Kato I. 1980. Protein inhibitors of proteinases. Ann. Rev. Biochem. 49: 593-626).

"Infestin-4 and modified Kazal-type serine protease inhibitors" within the above definition include polypeptides that have the natural amino acid sequence or SEQ ID 2 to 5 or 21 to 24. However, such definition also includes polypeptides with a slightly modified amino acid sequence, for instance, a modified N-terminal or C-terminal end including terminal amino acid deletions or additions as long as those polypeptides substantially retain the activity of the respective Kazal-type serine protease inhibitors. "Kazal-type serine protease inhibitor" within the above definition also includes natural allelic variations that may exist and occur from one individual to another. "Kazal-type serine protease inhibitor" within the above definition further includes variants of Kazal-type serine protease inhibitors. Such variants differ in one or more amino acid residues from the wild type sequence. Examples of such differences may include truncation of the N- and/or C-terminus by one or more amino acid residues (e.g. 1 to 10 amino acid residues), or addition of one or more extra residues at the N- and/or C-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in table 1.

TABLE 1

| (1) | Alanine | Glycine | | |
|---|---|---|---|---|
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophan | |

The invention further relates to a polynucleotide encoding a Kazal-type serine protease inhibitor as described in this application. The term "polynucleotide(s)" generally refers to any polyribonucleotide or polydeoxyribonucleotide that may be unmodified RNA or DNA or modified RNA or DNA. The polynucleotide may be single- or double-stranded DNA, single or double-stranded RNA. As used herein, the term "polynucleotide(s)" also includes DNAs or RNAs that comprise one or more modified bases and/or unusual bases, such as inosine. It will be appreciated that a variety of modifications may be made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells.

The skilled person will understand that, due to the degeneracy of the genetic code, a given polypeptide can be encoded by different polynucleotides. These "variants" are encompassed by this invention.

Preferably, the polynucleotide of the invention is an isolated polynucleotide. The term "isolated" polynucleotide refers to a polynucleotide that is substantially free from other nucleic acid sequences, such as and not limited to other chromosomal and extrachromosomal DNA and RNA. Isolated polynucleotides may be purified from a host cell. Conventional nucleic acid purification methods known to skilled artisans may be used to obtain isolated polynucleotides. The term also includes recombinant polynucleotides and chemically synthesized polynucleotides.

Yet another aspect of the invention is a plasmid or vector comprising a polynucleotide according to the invention. Preferably, the plasmid or vector is an expression vector. In a particular embodiment, the vector is a transfer vector for use in human gene therapy.

Still another aspect of the invention is a host cell comprising a polynucleotide of the invention or a plasmid or vector of the invention.

The host cells of the invention may be employed in a method of producing a Kazal-type serine protease inhibitor, which is part of this invention. The method comprises:
culturing host cells of the invention under conditions such that the Kazal-type serine protease inhibitor is expressed; and
optionally recovering the Kazal-type serine protease inhibitor from the culture medium.

Expression of the Proposed Polypeptides:

The Kazal-type serine protease inhibitors and the modified Kazal-type serine protease inhibitors of the invention may be produced as recombinant molecules in prokaryotic or eukaryotic host cells, such as bacteria, yeast, plant, animal (including insect) or human cell lines or in transgenic animals. Optionally, the polypeptides are secreted from the host cells.

Expression in Animal or Human Cell Lines

The production of recombinant proteins at high levels in suitable host cells requires the assembly of the above-mentioned modified cDNAs into efficient transcriptional units together with suitable regulatory elements in a recombinant expression vector that can be propagated in various expression systems according to methods known to those skilled in the art. Efficient transcriptional regulatory elements could be derived from viruses having animal cells as their natural hosts or from the chromosomal DNA of animal cells. Preferably, promoter-enhancer combinations derived from the Simian Virus 40, adenovirus, BK polyoma virus, human cytomegalovirus, or the long terminal repeat of Rous sarcoma virus, or promoter-enhancer combinations including strongly constitutively transcribed genes in animal cells like beta-actin or GRP78 can be used. In order to achieve stable high levels of mRNA transcribed from the cDNAs, the transcriptional unit should contain in its 3'-proximal part a DNA region encoding a transcriptional termination-polyadenylation sequence. Preferably, this sequence is derived from the Simian Virus 40 early transcriptional region, the rabbit beta-globin gene, or the human tissue plasminogen activator gene.

The cDNAs are then transfected into a suitable host cell line for expression of the therapeutic polypeptide. Examples of cell lines that can be used are monkey COS-cells, mouse L-cells, mouse C127-cells, hamster BHK-21 cells, human embryonic kidney 293 cells, and hamster CHO-cells.

The recombinant expression vector encoding the corresponding cDNAs can be introduced in several different ways. For instance, recombinant expression vectors can be created from vectors based on different animal viruses. Examples of these are vectors based on baculovirus, vaccinia virus, adenovirus, and preferably bovine papilloma virus.

The transcription units encoding the corresponding DNAs can also be introduced into animal cells together with another recombinant gene, which may function as a dominant selectable marker in these cells in order to facilitate the isolation of specific cell clones, which have integrated the recombinant DNA into their genome. Examples of this type of dominant selectable marker genes are Tn5 amino glycoside phosphotransferase, conferring resistance to geneticin (G418), hygromycin phosphotransferase, conferring resistance to hygromycin, and puromycin acetyl transferase, conferring resistance to puromycin. The recombinant expression vector encoding such a selectable marker can reside either on the same vector as the one encoding the cDNA of the desired protein, or it can be encoded on a separate vector which is simultaneously introduced and integrated to the genome of the host cell, frequently resulting in a tight physical linkage between the different transcription units.

Other types of selectable marker genes, which can be used together with the cDNA of the desired protein are based on various transcription units encoding dihydrofolate reductase (dhfr). After introduction of this type of gene into cells lacking endogenous dhfr-activity, preferentially CHO-cells (DUKX-B11, DG-44) it will enable these to grow in media lacking nucleosides. An example of such a medium is Ham's F12 without hypoxanthine, thymidin, and glycine. These dhfr-genes can be introduced together with the Kazal-type serine protease inhibitors' cDNA transcriptional units into CHO-cells of the above type, either linked on the same vector or on different vectors, thus creating dhfr-positive cell lines producing recombinant protein.

If the above cell lines are grown in the presence of the cytotoxic dhfr-inhibitor methotrexate, new cell lines resistant to methotrexate will emerge. These cell lines may produce recombinant protein at an increased rate due to the amplified number of linked dhfr and the desired protein's transcriptional units. When propagating these cell lines in increasing concentrations of methotrexate (1-10000 nM), new cell lines can be obtained which produce the desired protein at a very high rate.

The above cell lines producing the desired protein can be grown on a large scale, either in suspension culture or on various solid supports. Examples of these supports are micro carriers based on dextran or collagen matrices, or solid supports in the form of hollow fibres or various ceramic materials. When grown in cell suspension culture or on micro carriers the culture of the above cell lines can be performed either as a batch culture or as a perfusion culture with continuous production of conditioned medium over extended periods of time. Thus, according to the present invention, the above cell lines are well suited for the development of an industrial process for the production of the desired recombinant proteins.

The recombinant protein, which accumulates in the medium of secreting cells of the above types, can be concentrated and purified by a variety of biochemical and chromatographic methods, including methods utilizing differences in size, charge, hydrophobicity, solubility, specific affinity, etc. between the desired protein and other substances in the cell cultivation medium.

An example of such purification is the adsorption of the recombinant protein to a monoclonal antibody or a binding peptide, which is immobilised on a solid support. After desorption, the protein can be further purified by a variety of chromatographic techniques based on the above properties.

Expression in Yeast Expression Systems

Exemplary genera of yeast contemplated to be useful in the practice of the present invention as hosts are *Pichia* (formerly classified as Hansenula), *Saccharomyces, Kluyveromyces, Aspergillus, Candida, Torulopsis, Torulaspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis*, and the like. Genera include those selected from the group consisting of *Saccharomyces, Schizosaccharomyces, Kluyveromyces, Pichia* and *Torulaspora*. Examples of *Saccharomyces* spp. are *S. cerevisiae, S. italicus* and *S. rouxii*.

Suitable promoters for *S. cerevisiae* include those associated with the PGKI gene, GAL1 or GAL10 genes, CYCI, PHO5, TRPI, ADHI, ADH2, the genes for glyceral-dehyde-3-phosphate dehydrogenase, hexokinase, pyruvate decarboxylase, phos-phofructokinase, triose phosphate isomerase, phosphoglucose isomerase, glucokinase, alpha-mating factor pheromone, the PRBI, the GUT2, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (Maundrell K. 1990. Nmt1 of fission yeast. A highly transcribed gene completely repressed by thiamine. J. Biol. Chem. 265:10857-10864) and the glucose repressible jbpl gene promoter as described by Hoffman and Winston (Hoffman C S and Winston F. 1990. Isolation and characterization of mutants constitutive for expression of the fbp1 gene of *Schizosaccharomyces pombe*. Genetics 124:807-816).

The transcription termination signal may be the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* ADHI gene is optionally used.

Expression in Bacterial Expression Systems

Exemplary expression systems for the production of the modified Kazal-type serine protease inhibitors of the invention in bacteria include *Bacillus subtilis, Bacillus brevis, Bacillus megaterium, Caulobacter crescentus*, and, most importantly, *Escherichia coli* BL21 and *E. coli* K12 and their derivatives. Convenient promoters include but are not limited to trc promoter, tac promoter, lac promoter, lambda phage promoter p_L, the L-arabinose inducible araBAD promoter, the L-rhamnose inducible rhaP promoter, and the anhydrotetracycline-inducible tetA promoter/operator.

In one embodiment, polynucleotides encoding the Infestin and modified Kazal-type serine protease inhibitors of the invention may be fused to signal sequences which will direct the localization of a protein of the invention to particular compartments of a prokaryotic cell and/or direct the secretion of a protein of the invention from a prokaryotic cell. For example, in *E. coli*, one may wish to direct the expression of the protein to the periplasmic space. Examples of signal sequences or proteins (or fragments thereof) to which the proteins of the invention may be fused in order to direct the expression of the polypeptide to the periplasmic space of bacteria include, but are not limited to, the pelB signal sequence, the maltose binding protein signal sequence, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (New England Biolabs).

Expression in Plant Cells

Exemplary plant systems for expression of the modified Kazal-type serine protease inhibitors of the invention include tobacco, potato, rice, maize, soybean, alfalfa, tomato, lettuce and legume (summarized by Ma J K C et al. 2003. The production of recombinant pharmaceutical proteins in plants. Nat. Rev. Genet. 4:794-805). Expression of recombinant proteins in plant systems may be directed by suitable regulatory elements to specific organs or tissues such as fruits, seeds, leaves or tubers. Alternatively, proteins may be secreted from the roots. Within the cell, proteins may be targeted to particular compartments, e.g. the endoplasmic reticulum, protein bodies or plastids. There the product may accumulate to higher levels or undergo particular forms of posttranslational modification.

Transgenic Expression

Exemplary examples for large-scale transgenic expression systems (for review see Pollock D P. 1999. Transgenic milk as a method for the production of recombinant antibodies. J Immunol Methods 231:147-157) include rabbit (Chrenek P et al. 2007. Expression of recombinant human factor VIII in milk of several generations of transgenic rabbits. Transgenic Res. 2007 Jan. 31), goat (Lazaris A et al. 2006. Transgenesis using nuclear transfer in goats. Methods Mol Biol. 348:213-26), pig and cattle.

Purification and Therapeutic Formulation

It is preferred to purify the Kazal-type serine protease inhibitor of the present invention to greater than 80% purity, more preferably greater than 95% purity, and particularly preferred is a pharmaceutically pure state that is greater than 99.9% pure with respect to contaminating macromolecules, particularly other proteins and nucleic acids, and free of infectious and pyrogenic agents. Preferably, an isolated or purified Kazal-type serine protease inhibitor of the invention is substantially free of other polypeptides.

The present invention provides the use of such an inhibitor described herein in medicine; and also the use of such an inhibitor in the manufacture of a medicament. Therefore, according to another aspect of the present invention, a pharmaceutical formulation is provided comprising this inhibitor, which is suitable for inhibiting the activation of factor XII or the activity of factor XIIa and which prevents the formation and/or the stabilization of three-dimensional arterial or venous thrombi.

The therapeutic polypeptides described in this invention can be formulated into pharmaceutical preparations for therapeutic use. The purified proteins may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). In particular, the pharmaceutical composition comprising the polypeptide of the invention may be formulated in lyophilized or stable soluble form. The polypeptide may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially the compositions of the invention are administered systemically. For systemic use, the therapeutic proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential route of administration is intravenous administration. The formulations can be administered continuously by infusion or by bolus injection. Some formulations encompass slow release systems.

Tablets and capsules for oral administration may contain conventional excipients such as binding agents, fillers, lubricants and wetting agents, etc. Oral liquid preparations may be in the form of aqueous or oily suspensions, solutions, emulsions, syrups, elixirs or the like, or may be presented as a dry product for reconstitution with water or other suitable vehicle for use. Such liquid preparations may contain conventional additives, such as suspending agents, emulsifying agents, non-aqueous vehicles and preservatives.

Formulations suitable for topical application may be in the form of aqueous or oily suspensions, solutions, emulsions, gels or, preferably, emulsion ointments. Formulations useful for spray application may be in the form of a sprayable liquid or a dry powder.

The Kazal-type serine protease inhibitor polypeptides of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, and mode of administration and has to be determined in preclinical and clinical trials for each respective indication.

The pharmaceutical composition of the invention may be administered alone or in conjunction with other therapeutic agents. These agents may be incorporated as part of the same pharmaceutical.

The various products of the invention are useful as medicaments. Accordingly, the invention relates to a pharmaceutical composition comprising a Kazal-type serine protease inhibitor polypeptide as described herein, a polynucleotide of the invention, or a plasmid or vector of the invention.

The modified DNAs of this invention may also be integrated into a transfer vector for use in the human gene therapy.

The nature, benefit, and further features of the present invention become apparent from the following detailed description of the performed experiments and their results when considered in conjunction with the accompanying figures described below.

FIGURES

FIG. 1: Model of pathogenic thrombosis as discussed by Colman (Colman R W. 2006. Are hemostasis and thrombosis two sides of the same coin? J. Exp. Med. 203:493-495).

FIG. 2: Amino acid sequence similarity between Infestin-4 (I4) and SPINK-1 (SP) *, identical; |, similar amino acid FIG. 3: Contact sites of R. prolixus inhibitor with thrombin are indicated by # and contact sites of SPINK-1 with chymotrypsin by +.

FIG. 4: Amino acid sequences of Infestin-4, SPINK1 and three SPINK1 mutants (K1-K3); * denotes identical; | similar amino acids with regard to the Infestin-4 sequence. The underlined sequence of I4 was used to replace 15 amino acids of SPINK-1 to generate mutant K1. Mutants K2 and K3 were generated by additional point mutations (amino acids underlined) on the K1 sequence.

Figure 5:
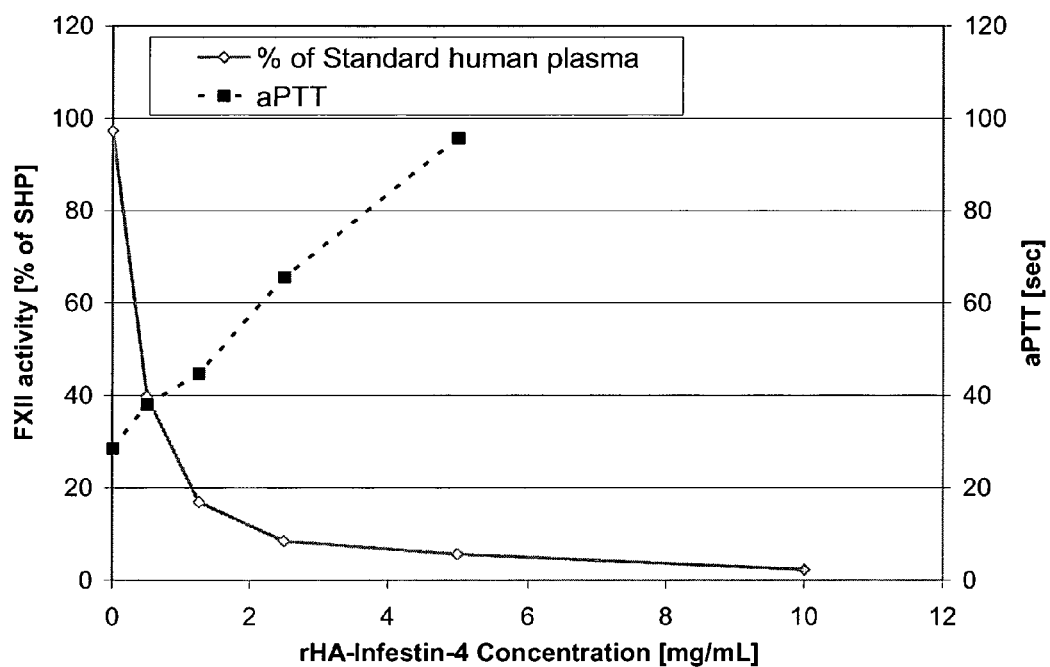

FIG. 5: Effect of rHA-Infestin-4 in vitro on aPTT and FXII activity in mouse plasma FIG. 6: Prolongation of aPTT following 100 and 200 mg/kg rHA-Infestin-4 (i.v.) in mice (prior to administration and) up to 4.5 hours FIG. 7: Inhibition of FXII following 100 and 200 mg/kg rHA-Infestin-4 (i.v.) in mice (prior to administration and) up to 4.5 hours FIG. 8: Time course of rHA-Infestin-4 in mouse plasma following i.v. injection of 100 mg/kg (mean; n=1-2/time point)

FIG. 9: Comparison of pharmacokinetics of (His)6-Infestin and rHA-Infestin-4 in mice FIG. 10: Effect of rHA-Infestin-4 on time to hemostasis (n=10-15/group, mean±SD)

FIG. 11: Effect of rHA-Infestin-4 on total blood loss (n=10-15/group, mean±SD)

FIG. 12: Effect of rHA-Infestin-4 on time to hemostasis (n=10-15/group, individual data)

FIG. 13: Effect of rHA-Infestin-4 on total blood loss (n=10-15/group, individual data)

EXAMPLES

Example 1

Cloning of Infestin-4, SPINK-1 and Modified Kazal-Type Serine Protease Inhibitors The SPINK-1 amino acid sequence was back translated into a cDNA sequence optimized for mammalian cell expression and including suitable restriction sites. The nucleotide sequences of the SPINK molecules to be generated (see FIG. 4) including the native SPINK-1 signal peptide were divided into 3 segments, each of which was custom synthesized by overlapping oligonucleotides (Medigenomix, Martinsried, Germany). Two variants of segments 2 and 3, respectively were generated and assembled in the following way:
S1+S2 wt+S3 wt resulted in SPINK-1 wild-type
S1+S2K1+S3 wt resulted in SPINK-K1
S1+S2K1+S3K3 resulted in SPINK-K3

Nucleotide sequences of segments are given as SEQ-ID NO 7 to 11 (S1, SEQ ID NO 7; S2 wt, SEQ ID NO 8; S2K1, SEQ ID NO 9; S3 wt, SEQ ID NO 10; S3K3, SEQ ID NO 11).

The assembly of segments was performed as follows. Segments, obtained from Medigenomix in cloning vector pCR2.1 (Invitrogen), were cut out by restriction endonucleases EcoRI/NarI (S1), NarI/KpnI (S2 wt and S2K1) and KpnI/BamH1 (S3 wt and S3K3), respectively, isolated from agarose gels and ligated into EcoRI/BamH1 digested expression vector pIRESpuro3 (BD Biosciences) in the following combinations:
a) S1 EcoRI/NarI+S2 wt NarI/KpnI+S3 wt KpnI/BamH1
b) S1 EcoRI/NarI+S2K1 NarI/KpnI+S3 wt KpnI/BamH1
c) S1 EcoRI/NarI+S2K1 NarI/KpnI+S3K3 KpnI/BamH1
resulting in plasmids p1171 (a), p1172 (b) and p1174 (c), respectively.

To generate the SPINK-K2 sequence, plasmid p1174 was subjected to a site directed mutagenesis reaction with a commercially available mutagenesis kit (QuickChange XL Site Directed Mutagenesis Kit, Stratagene) using oligonucleotides We2450 and We2451 (SEQ ID NO 12 and 13) according to the manufacture's protocol. The resulting plasmid was called p1173.

The Infestin-4 sequence was assembled from p1174 (the N-terminal part of SPINK-K3) and the coding sequence for the C-terminal part (fragment I4C, SEQ ID NO 14), which was custom synthesized by overlapping oligonucleotides (Medigenomix, Martinsried, Germany). First, the EcoRI/BamH1 fragment containing the coding sequence for the SPINK-K3 N-terminus was isolated from p1174 and cloned into an EcoRI/BamH1 linearized pIRESpuro3. The resulting plasmid was subsequently digested with BamH1 and NotI and a BglII/NotI fragment isolated from the pCR2.1 vector containing the coding sequence for the I4C fragment (as supplied by Medigenomix) was inserted. The resulting plasmid called p1288 now contained the coding sequence for Infestin-4.

For purification purposes an expression vector attaching a hexahistidine tag to Infestin-4 was constructed. For such purpose an insertion mutagenesis was performed using a commercially available mutagenesis kit (QuickChange XL Site Directed Mutagenesis Kit, Stratagene) under conditions described by the kit manufacturer using p1288 as template and oligonucleotides We2973 and We2974 (SEQ ID NO 26 and 27) as mutagenic primers. The resulting plasmid was called p1481 coding for an Infestin-4 sequence with a C-terminal extension of an 8 amino acid glycine/serine linker and a stretch of 6 histidine residues (SEQ ID NO 28).

Example 2

Cloning of Albumin Fusion Constructs

First, the human albumin cDNA sequence, cloned into the EcoRI site of pIRE-Spuro3 (BD Biosciences), was mutagenized by site directed mutagenesis with a commercially available mutagenesis kit (QuickChange XL Site Directed Mutagenesis Kit, Stratagene) using oligonucleotides We2467 and We2468 (SEQ ID NO 15 and 16) to remove the stop codon and to introduce a first part of a glycine/serine linker and a BamH1 restriction site for insertion of the SPINK and Infestin-4 sequences. The resulting plasmid was called p1192. The SPINK coding sequences (without signal peptide) were amplified by PCR using p1171, p1172, p1173 and p1174 as templates and oligonucleotides We2470 and We2473 (SEQ ID NO 17 and 18) introducing the remaining part of the glycine/serine linker and a BamH1 site at the 5'-end and a NotI site at the 3'-end as primers. The PCR fragments were digested with BamH1/NotI, purified and inserted into p1192, also cut with BamH1/NotI. The resulting albumin fusion plasmid p1187 contained SPINK-1 wild-type fused to albumin, p1188 SPINK-K1 fused to albumin, p1189 SPINK-K2 fused to albumin, and p1190 SPINK-K3 fused to albumin. Similarly the Infestin-4 albumin expression plasmid was constructed, but instead primers We2473 and We2623 (SEQ ID NO 18 and 19) were used on p1288. The resulting expression plasmid was called p1290. The amino acid sequences of the encoded proteins are given as SEQ ID NO 20, 21, 22, 23 and 24, respectively.

Example 3

Transfection and Expression of His-Tagged Infestin-4 and Infestin-4 and SPINK Albumin Fusion Proteins in Mammalian Cell Culture Expression plasmids were grown up in *E. coli* TOP10 (Invitrogen) and purified using standard protocols (Qiagen). HEK-293 cells were transfected using the Lipofectamine 2000 reagent (Invitrogen) and grown up in serum-free medium (Invitrogen 293 Express) in the presence of 4 µg/ml Puromycin. Transfected cell populations were spread through T-flasks into roller bottles or small-scale fermenters from which supernatants were harvested for purification. Expression yields in HEK-293 cells were between 6 and 15 µg/mL for the albumin fusion proteins and about 0.5 to 1 µg/mL für His-tagged Infestin-4.

Example 4

Expression of His-Tagged Infestin-4 and Infestin-4 Albumin Fusion Proteins in Yeast Coding sequences of His-tagged Infestin-4 and Infestin-4 albumin fusion protein were transferred into expression vectors suitable for *S. cerevisiae* expression as described by Invitrogen, MoBiTec or Novozymes Biopharma. Expression in shake flask cultures using standard growth media resulted in expression yields between 30 and 50 µg/mL for the albumin fusion protein and about 1 to 5 µg/mL für His-tagged Infestin-4 as estimated from SDS PAGE analysis after Coomassie stain.

Example 5

Purification of the Kazal Inhibitor-Albumin Fusion Proteins

25 L of the 0.2 µm filtered cell culture supernatant were concentrated to a volume of 1 L by ultra filtration (10 kDa exclusion size) and subsequently diafiltrated against 40 mM Tris/HCl pH 7.5 and again 0.2 µm filtered. The crude concentrate was further purified by anion exchange chromatography using POROS 50 PI (26×750). The column was equilibrated with 40 mM Tris/HCl pH 7.5. After loading a 15 column volumes (CV) wash step was performed. The product was eluted in a linear gradient over 35 CV to 40 mM Tris/HCl 1200 mM sodium chloride pH 7.5. Fusion protein containing fractions were pooled and concentrated by ultrafiltration. A diafiltration against physiological sodium chloride solution led to an about 90% pure product with a concentration of about 15 mg/mL.

Purification and detection of His-tagged Infestin-4 may be accomplished by using commercially available kits (e.g. His-tag Purification and Detection Kit; Qiagen, Hilden, Germany) containing Ni-NTA resin for purification and PentaHis antibodies for detection of His-tagged proteins.

Example 6

Biochemical Characterization of Kazal Inhibitor-Albumin Fusion Proteins

Determination of the Identity/Purity:

The identity/purity of the protein was determined by SDS-PAGE (8-16%) using standard procedure (NOVEX). The staining was performed by Coomassie Blue.

Protein Concentration:

The protein concentration of an albumin fusion protein was determined using an albumin specific ELISA, the principal performance of which is known to those skilled in the art. Briefly, microplates were incubated with 120 µL per well of the capture antibody (rabbit anti human albumin IgG, DAKO A0001) diluted 1:14000 in buffer A (Sigma C-3041) overnight at ambient temperature. After washing plates three times with buffer B (Sigma T-9039), each well was incubated with 200 µL buffer C (Sigma T-8793) for one hour at ambient temperature. After another three wash steps with buffer B, serial dilutions of the test samples in buffer B as well as serial dilutions of N Protein Standard SL (Dade Behring, 0.5-100 ng/mL) in buffer B (volumes per well: 100 µL) were incubated for one hour at ambient temperature. After three wash steps with buffer B, 100 µL of a 1:12500 dilution in buffer B of the detection anti-body (rabbit anti human albumin, DAKO P0356, peroxidase labelled) were added to each well and incubated for another hour at ambient temperature. After three wash steps with buffer B, 100 µL of substrate solution (TMB, Dade Behring, OUVF) were added per well and incubated for 30 minutes at ambient temperature in the dark. Addition of 100 µL stop solution (Dade Behring, OSFA) prepared the samples for reading in a suitable microplate reader at 450 nm wavelength. Concentrations of test samples were then calculated using the standard curve with N Protein Standard as a reference.

Determination of the Activated Partial Thromboplastin Time

The activated partial thromboplastin time was determined in standard human plasma (SHP, Dade Behring), where different amounts of the respective inhibitor were added into an imidazole buffer to a total volume of 200 µL. 50 µL of this solution were added to 50 µL Pathromtin SL (Dade Behring) and incubated for 120 sec at 37° C. Subsequently, 50 µL of a calcium chloride solution (25 mM) were added to start the reaction.

The procedure was performed in a BCT (Behring Coagulation Timer) according to the conditions suggested by the manufacture.

Determination of the Prothrombin Time:

The prothrombin time was determined in standard human plasma (Dade Behring), the activation reagent was Thromborel S (Dade Behring). 100 µl Thromborel S were added to 50 µL sample (see above) after 15 sec incubation time. The procedure was performed in a BCT (Behring Coagulation Timer) according to the conditions suggested by the manufacture.

Results:

TABLE 2

Activity of Infestin-4 and SPINK mutant albumin fusions in vitro

| | pmol | APTT [sec] | PT [sec] | Purity*** |
|---|---|---|---|---|
| rHA-Infestin-4[1] | 4000** | 102 | 13.4 | 85% |
| | 6000** | >240 | 14.2 | |
| rHA-SPINK-K3[2] | 2600**** | 43 | 12.6 | 90% |
| | 6500**** | 60 | 13.1 | |
| | 13000**** | 99 | 13.9 | |
| rHA-SPINK-K2[3] | 3000**** | 51 | 13.0 | >90% |

*test volume 200 µl: 150 µl standard human plasma + 50 µl imidazole
**determined by Albumin specific ELISA
***estimated by SDS-PAGE
****determined by OD 280, ε [%] = 6.67
[1,2,3] derived from [1]p1290, [2]p1190 and [3]p1189

These experiments demonstrate that Kazal-type inhibitors are able to inhibit the intrinsic pathway with almost no impact on the extrinsic pathway expressed by the almost constant PT.

Example 7

Infestin-4 Albumin Fusion is Highly Efficacious in Preventing Vessel Occlusion in a Mouse Model for Arterial Thrombosis To estimate the dose required for achieving a potent protection of mice from arterial thrombosis, exploratory in vitro spiking experiments were performed. Spiking rHA-Infestin-4 into mouse plasma resulted in a decreased FXII activity and a prolongation of the aPTT, whereas PT remained virtually unchanged.

TABLE 3

Effect of rHA-Infestin-4 spiked into mouse plasma on aPTT and FXII activity

| rHA-Infestin-4 concentration [mg/mL] | aPTT [sec.] | FXII activity [% of the norm] |
|---|---|---|
| 0 | 28.5 | 97.3 |
| 0.5 | 38.0 | 39.8 |
| 1.25 | 44.7 | 17.0 |
| 2.5 | 65.6 | 8.5 |
| 5 | 95.7 | 5.6 |
| 10 | not determined | 2.3 |

TABLE 4

Effect of rHA-Infestin-4 spiked into mouse plasma on PT and FXII activity

| rHA-Infestin-4 concentration [mg/mL] | PT [sec.] | FXII activity [% of the norm] |
|---|---|---|
| 0 | 10.6 | 71.5 |
| 3.3 | 10.1 | 12.0 |

Figure 6:
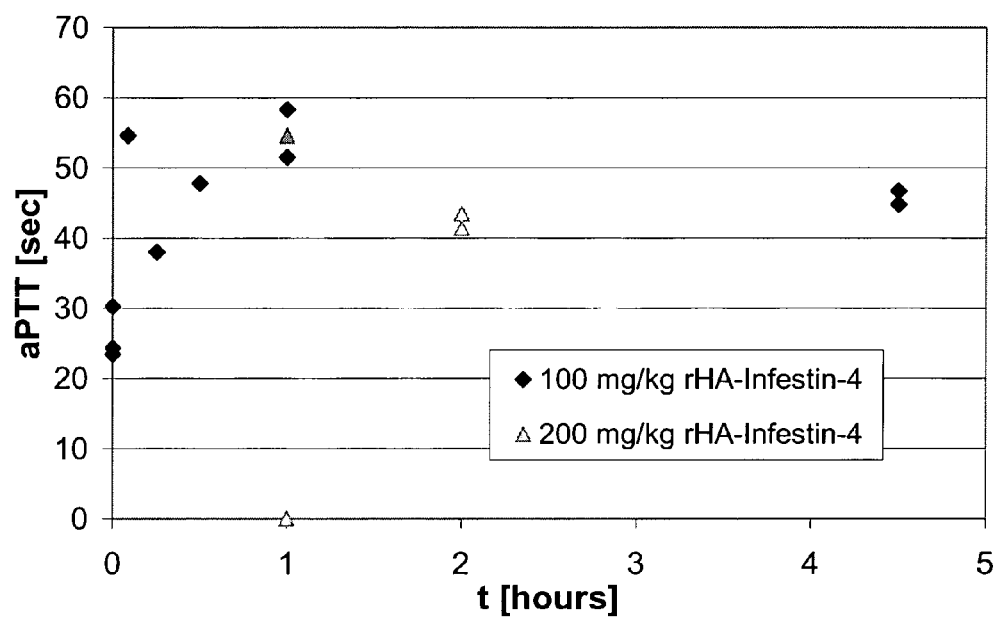
Figure 7:
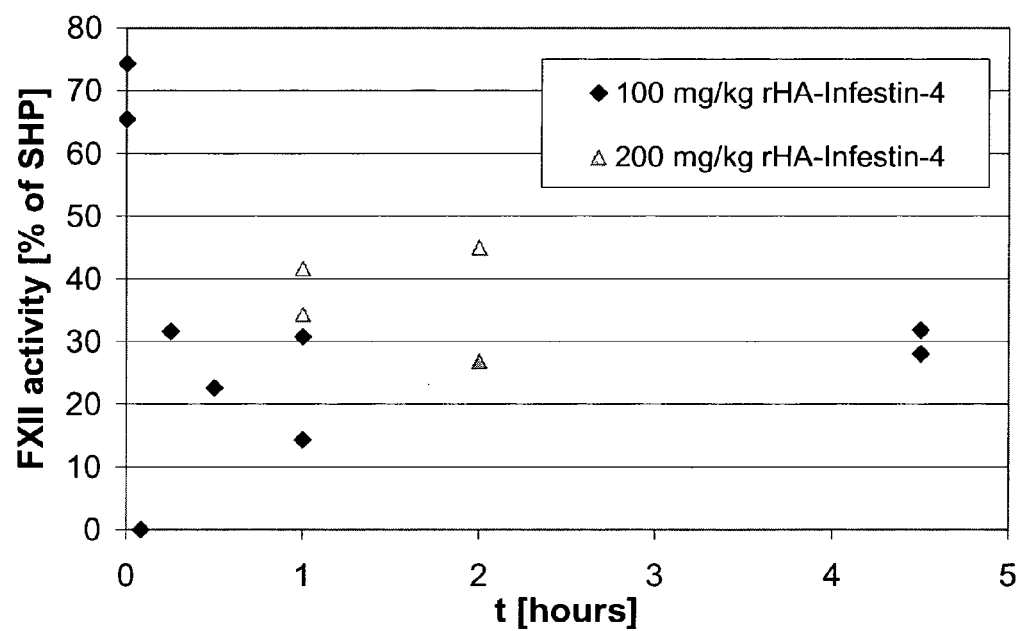
Figure 8:
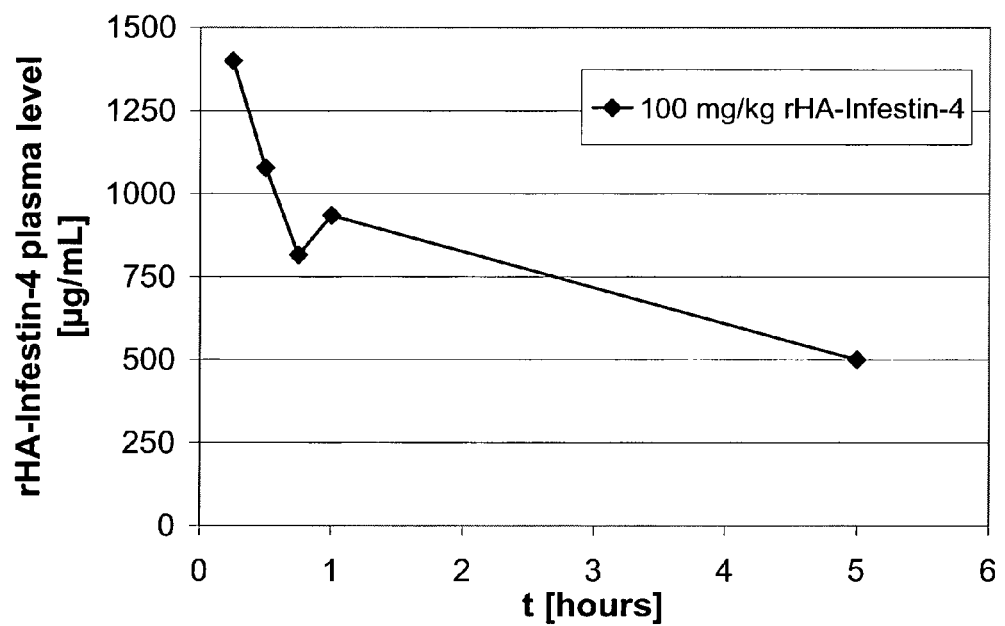

As a very pronounced FXII inhibition was observed following spiking of mouse plasma in vitro, mice were treated i.v. with rHA-Infestin-4 and the time course of aPTT and FXII activity was assessed (FIGS. 6 and 7). In addition, the plasma levels of rHA-Infestin-4 were determined at the time points specified in table 5.

TABLE 5

Effect of rHA-Infestin-4 on aPTT and FXII activity

| Treatment | t [min.] | aPTT [sec.] | FXII activity [% of the norm] | rHA-Infestin-4 [µg/mL] |
|---|---|---|---|---|
| rHA-Infestin-4, 100 mg/kg | 0 | 26.0 | 69.9 | <0.04 |
| | 5 | 54.6 | n.d. | n.d. |
| | 15 | 38.0 | 31.6 | 1399.3 |
| | 30 | 47.8 | 22.6 | 1077.8 |
| | 60 | 54.9 | 22.5 | 934.4 |
| | 270 | 45.8 | 29.9 | 499.4 |
| rHA-Infestin-4, 200 mg/kg | 60 | 54.6 | 38.0 | 1847 |
| | 120 | 42.5 | 35.9 | 1245.9 |
| rHA-Infestin-4, 2 × 100 mg/kg | 150 | 64.0 | 22.0 | 1189.3 |
| rHA-Infestin-4, 400 mg/kg | 30 | 49.4 | 12.6 | n.d. |
| | 90 | 44.8 | 27.5 | n.d. |
| rHA-Infestin-4, 800 mg/kg | 30 | 52.1 | 11.1 | n.d. |
| | 90 | 36.0 | 28.2 | n.d. |

These experiments showed that with a single i.v. injection of 400 mg/kg of rHA-Infestin-4 the aPTT was prolonged and FXII activity was decreased for at least one hour. A single injection should therefore be able to protect mice from thrombotic vessel occlusion in the $FeCl_3$ model of thrombosis. Accordingly, animals were treated with 400 mg/kg of rHA-Infestin-4 i.v. and the rate of vessel occlusion was determined, as well as the time until the occlusion occurred.

Animals received rHA-infestin-4 by a single i.v. injection of doses up to 400 mg/kg at t=0. For the assessment of arterial thrombosis the arteria abdominalis was exposed in deep anesthesia. Baseline blood flow was determined by placing an ultrasonic flow probe around the vessel. To initiate thrombosis a 0.5 mm² patch of filter paper, which was saturated with 10% ferric chloride solution, was placed on the arteria abdominalis downstream of the flow probe. After an exposure period of 3 minutes, the filter paper was removed and the blood flow was monitored for 60 minutes to determine the occurrence of thrombotic occlusions.

Table 6 shows that 82% of the vehicle treated animals showed thrombosis. In contrast none of the 10 mice treated with rHA-Infestin-4 developed thrombosis. This effect was dose-dependent and inverse to the decreasing occlusion incidence, the time until occurrence of occlusion increased.

TABLE 6

Thrombotic occlusion rate following a single i.v. treatment with up to 400 mg/kg of rHA-Infestin-4

| No. | Treatment | n | Occlusion rate | Time to occlusion [min.; mean ± SD] |
|---|---|---|---|---|
| 1 | Isotonic saline | 21 | 19 (91%) | 10.1 ± 3 |
| 2 | rHA-Infestin-4 50 mg/kg | 10 | 7 (70%) | 15.0 ± 7.6 |
| 3 | rHA-Infestin-4 93.2 mg/kg | 10 | 2 (20%) | 23.5 ± 12.0 |
| 4 | rHA-Infestin-4 186.3 mg/kg | 10 | 1 (10%) | 48.0 ± 0.0 |
| 5 | rHA-Infestin-4 400 mg/kg | 10 | 0 (0%) | not applicable (no occlustion occurred) |

As FXII k.o. animals are similarly protected from thrombosis, but in parallel no hemostasis deficiency is observed, hemostasis was analysed in a similar manner in mice treated intravenously with up to 400 mg/kg of rHA-Infestin-4. For this purpose animals were anesthetized with Narcoren by a single i.v. injection of about 60 mg/kg. rHA-Infestin-4 is injected 15 minutes prior to lesion of the animal, i.e. at the same time point and with the same dose as in the experiment to assess its anti-thrombotic effects.

Hemostasis was quantified by determining the time to hemostasis and the blood loss until occurrence of hemostasis, with the end of the 30 minutes observation period as censor. The volume of total blood loss was calculated by measuring the HGB present in the saline used for submersion of the tail tip. The HGB of the animals was taken into consideration accordingly. The tail tip cut was performed with a scalpel knife under deep anesthesia, removing about 3 mm of the tail tip. Immediately upon lesion, the tail tip was submerged in pre-warmed saline, which was also kept at the physiological body temperature of the mice using a water bath during the observation period. The observation period to monitor bleeding was 30 min. All test articles were administered i.v. at 15 min prior to the start of the observation period (tail cut).

All key parameters for hemostasis within the observation period, time to hemostasis and blood loss did not show obvious differences between the two treatment groups and the vehicle control group (Table 7, 8, FIGS. 10-13).

TABLE 7

Descriptive statistics for Frequency and Time to Hemostasis within 30 minutes (n = 10-15/group)

| Treatment | Frequency of hemostasis | Time to hemostasis | | | |
| --- | --- | --- | --- | --- | --- |
| | | Mean ± SD (sec.) | Min. (sec.) | Med. (sec.) | Max. (sec.) |
| Vehicle | 15/15 (100%) | 165 ± 176 | 80 | 100 | 660 |
| rHA-Infestin-4 190 mg/kg | 10/10 (100%) | 114 ± 77 | 50 | 83 | 240 |
| rHA-Infestin-4 400 mg/kg | 10/10 (100%) | 115 ± 35 | 80 | 100 | 180 |

TABLE 8

Descriptive statistics for Blood loss (n = 10-15/group)

| Treatment | Mean ± SD (μL) | Min. (μL) | Median (μL) | Max. (μL) |
| --- | --- | --- | --- | --- |
| Vehicle | 9.6 ± 7.4 | 1.4 | 8.1 | 23.7 |
| rHA-Infestin-4 190 mg/kg | 3.9 ± 2.7 | 1.1 | 3.1 | 8.9 |
| rHA-Infestin-4 400 mg/kg | 16.1 ± 14.3 | 2.6 | 11.9 | 49.1 |

Infestin-4 only, i.e. without being fused to albumin (e.g. see example 1, His-tagged infestin-4), is tested for potential protection from thrombosis. A dose approximately equimolar to 400 mg/kg rHA-Infestin-4 is injected i.v. into mice once at 15 minutes prior to induction of thrombosis. Induction and assessment of thrombosis are performed in an identical manner as described for the rHA-infestin-4. To overcome the rapid elimination Infestin-4 is applied by continuous infusion or repeated injections, a standard procedure to achieve a high plasma level of compounds being cleared rapidly from circulation or losing activity due to mechanisms different than pharmacokinetic reasons.

The results show that the rHA-infestin-4 treated mouse group shows now thrombosis nor bleeding risk which matches the result (shown elsewhere) of the FXII k. o. mouse group.

Example 8

Effects of Commercially Available FXII(a) Inhibitor Berinert® P on aPTT, PT and Vessel Occlusion in the Rat $FeCl_3$ Model of Arterial Thrombosis In order to assess the suitability of the commercially available FXII(a) inhibitor Berinert® P (C1 esterase inhibitor) on its potential to inhibit FXII(a) several in vitro and in vivo experiments were performed.

The goal of the experiments was to determine the effects on aPTT and PT as well as on FXII activity in rat plasma and to assess the potential anti-thrombotic effects in a rat $FeCl_3$ model of arterial thrombosis.

Rats were anesthetized and blood samples were drawn retro-orbitally and processed to plasma for the determination of Factor XII activity according to standard procedures. Such plasma samples were spiked with Berinert© P and tested directly for FXII activity.

Berinert© P spike was tested for its effects on FXII activity in vitro. At high concentrations substantial FXII inhibition was observed (table 9).

TABLE 9

Effect of Berinert © P - spike into rat plasma on FXII activity

| Berinert © P concentration [U/mL] | FXII activity [% of the norm] |
| --- | --- |
| 0.98 | 215 |
| 2.4 | 94 |
| 4.5 | 85 |
| 9.92 | 55 |
| 16.7 | 25 |

As a significant inhibition of FXII was achieved, in vivo experiments were performed. Rats were treated i.v. with Berinert© P at a dose of 1200 U/kg in order to determine the potential prevention of thrombosis. The dose was chosen to result in a plasma concentration of 10-15 U/mL. For the assessment of arterial thrombosis the arteria carotis and venae jugularis were exposed in deep anesthesia. A cannula was inserted into the jugular vein for drug administration. To monitor blood flow, an ultrasonic flow probe was placed around the arteria carotis. To initiate thrombosis a 2.5 $mm^2$ patch of filter paper, which was saturated with 35% ferric chloride solution, was placed on the arteria carotis downstream of the flow probe. After an exposure of 3 minutes, the filter paper was removed and the blood flow was monitored for 60 minutes to determine the occurrence of thrombotic occlusions. APTT, PT and FXII activity were determined at the end of the observation period.

The 3 min treatment of the arteria carotis with 35% ferric chloride resulted in a 100% rate of thrombotic occlusions (table 10). Although a high dose of Berinert® P had resulted in an increased aPTT and moderate FXII inhibition, no positive effect on the occlusion rate was observed.

TABLE 10

| | | | Occlusion rates | | | |
|---|---|---|---|---|---|---|
| No. | Treatment | n | Occlusion rate | aPPT [mean ± SD] | PT [mean ± SD] | FXII activity [mean ± SD] |
| 1 | Isotonic saline | 10 | 10 (100%) | 22 ± 4 | 11.7 ± 1.5 | 121 ± 9 |
| 2 | Berinert ® P | 11 | 9 (82%) | 53 ± 9 | 12.0 ± 0.9 | 94 ± 14 |

Summary:

High concentrations of Berinert® P resulted in a pronounced inhibition of FXII in vitro. However, in the $FeCl_3$ model of arterial thrombosis even a high dose of Berinert® P was inefficient. This dose of Berinert® P was close to the technical limit as the application of higher doses would have resulted in a high protein load and non-physiological injection volumes.

Example 9

Comparison of Pharmacokinetics of (His)6-Infestin and rHA-Infestin-4 in Mice

His-tagged Infestin-4 ((His)6-Infestin-4) or Infestin-4 albumin fusions (rHA-Infestin-4) preparations were administered intravenously to a total of 28 NMRI mice. For (His)6-Infestin-4 the dose was 20 mg/kg body weight and 200 mg/kg body weight for rHA-Infestin-4 respectively. These doses correspond to an equivalent amount of the active component of the two proteins, i.e. Infestin-4.

Blood samples were drawn at appropriate intervals starting at 5 minutes after application of the test substances. Infestin-4 antigen content was subsequently quantified by an ELISA assay specific for Infestin-4. The mean values of the treatment groups were used for calculation. Half-lives for each protein were calculated using the time points of the beta phase of elimination according to the formula $t_{1/2}=\ln2/k$, whereas k is the slope of the regression line. The result is depicted in FIG. 9 (n=1-4/timepoint; mean).

The terminal half-life calculated for rHA-Infestin-4 is 3 h whereas the terminal half-life calculated for (His)6-Infestin-4 is 0.3 h. Therefore, a clear increase of the terminal half-life is shown for the rHA-Infestin-4 by a factor of 10 compared to (His)6-Infestin-4.

The invention claimed is:

1. A polypeptide comprising Infestin-4 or an Infestin-4 fragment with 1 to 10 amino acids deleted from the N- or C-terminus, wherein the Infestin-4 or Infestin-4 fragment is linked to at least one half-life enhancing polypeptide, and wherein the polypeptide inhibits Factor XIIa and prolongs clotting time in an aPTT assay.

2. The polypeptide of claim 1, wherein said polypeptide comprises Infestin-4 linked to at least one half-life enhancing polypeptide.

3. The polypeptide of claim 2, wherein said polypeptide comprises Infestin 3-4 linked to at least one half-life enhancing polypeptide.

4. The polypeptide of claim 1, wherein the at least one half-life enhancing polypeptide comprises at least one of albumin, afamin, alpha-fetoprotein, vitamin D binding protein, an immunoglobulin, or an Fc portion of an immunoglobulin.

5. The polypeptide of claim 4, wherein the at least one half-life enhancing polypeptide is albumin.

6. The polypeptide of claim 5, wherein the albumin is human albumin.

7. The polypeptide of claim 4, wherein the at least one half-life enhancing polypeptide is an IgG Fc portion.

8. The polypeptide of claim 1, wherein the at least one half-life enhancing polypeptide is linked to Infestin-4 or the Infestin-4 fragment via at least one linker.

9. The polypeptide of claim 8, wherein the at least one linker is a cleavable linker.

10. The polypeptide of claim 9, wherein the cleavable linker is cleavable by Factor XIIa.

11. A pharmaceutical composition comprising the polypeptide of claim 1 and at least one pharmaceutically acceptable carrier.

12. A method for increasing the half-life of Infestin-4 or of an Infestin-4 fragment in vivo comprising linking a polypeptide comprising Infestin-4 or an Infestin-4 fragment with 1 to 10 amino acids deleted from the N- or C-terminus to at least one half-life enhancing polypeptide.

13. A method of producing the polypeptide of claim 1 comprising expressing recombinant DNA encoding said polypeptide in eukaryotic cells, bacteria, yeasts, plant cells, insect cells, or transgenic animals.

14. A method of treating a condition or disorder related to arterial thrombus formation comprising administering an effective amount of the polypeptide of claim 1.

15. A method of treating arterial thrombosis, stroke, myocardial infarction, inflammation, complement activation, fibrinolysis, angiogenesis, pathological kinin formation, hypotonic shock, edema, hereditary angioedema, bacterial infections, arthritis, pancreatitis, articular gout, Disseminated Intravasal Coagulation (DIC), or sepsis comprising administering an effective amount of the polypeptide of claim 1.

16. A method of treating a condition or disorder related to arterial thrombus formation comprising administering an effective amount of the polypeptide of claim 5.

17. A method of treating arterial thrombosis, stroke, myocardial infarction, inflammation, complement activation, fibrinolysis, angiogenesis, pathological kinin formation, hypotonic shock, edema, hereditary angioedema, bacterial infections, arthritis, pancreatitis, articular gout, Disseminated Intravasal Coagulation (DIC), or sepsis comprising administering an effective amount of the polypeptide of claim 5.

* * * * *

SEQUENCE LISTING

```
<160> NUMBER OF SEQ ID NOS: 26

<210> SEQ ID NO 1
<211> LENGTH: 56
<212> TYPE: PRT
<213> ORGANISM: Homo sapiens

<400> SEQUENCE: 1

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 2
<211> LENGTH: 53
<212> TYPE: PRT
<213> ORGANISM: Artificial
<220> FEATURE:
<223> OTHER INFORMATION: Synthetic polypeptide

<400> SEQUENCE: 2

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50
```

```
<210> SEQ ID NO 3
<211> LENGTH: 53
<212> TYPE: PRT
<213> ORGANISM: Artificial
<220> FEATURE:
<223> OTHER INFORMATION: Synthetic polypeptide

<400> SEQUENCE: 3

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Cys Ala Glu Asn Arg Lys Arg Gln Thr Ser Ile Leu Ile Gln
            35                  40                  45

Lys Glu Gly Pro Cys
        50

<210> SEQ ID NO 4
<211> LENGTH: 54
<212> TYPE: PRT
<213> ORGANISM: Artificial
<220> FEATURE:
<223> OTHER INFORMATION: Synthetic polypeptide

<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
                20                  25                  30

Met Leu Asn Cys Ala Glu Asn Arg Lys Arg Gln Thr Ser Ile Leu Ile
            35                  40                  45

Gln Lys Glu Gly Pro Cys
        50

<210> SEQ ID NO 5
<211> LENGTH: 48
<212> TYPE: PRT
<213> ORGANISM: Triatoma infestans

<400> SEQUENCE: 5

Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
                20                  25                  30

Ala Gln Thr Lys Val Pro Gly Leu Lys Leu Val His Glu Gly Arg Cys
            35                  40                  45

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60
```

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                     85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                    565                 570                 575
Ala Ala Ser Gln Ala Ala Leu Gly Leu
            580                 585

<210> SEQ ID NO 7
<211> LENGTH: 81
<212> TYPE: DNA
<213> ORGANISM: Artificial
<220> FEATURE:
<223> OTHER INFORMATION: Synthetic oligonucleotide

<400> SEQUENCE: 7
gaattcgcca ccatgaaggt gaccggcatc ttcctgctgt ccgccctggc cctgctgtcc      60
ctgtccggca caccggcgc c                                                 81

<210> SEQ ID NO 8
<211> LENGTH: 84
<212> TYPE: DNA
<213> ORGANISM: Artificial
<220> FEATURE:
<223> OTHER INFORMATION: Synthetic oligonucleotide

<400> SEQUENCE: 8
ggcgccgact ccctgggccg cgaggccaag tgctacaacg agctgaacgg ctgcaccaag      60
atctacgacc ccgtgtgcgg tacc                                             84

<210> SEQ ID NO 9
<211> LENGTH: 75
<212> TYPE: DNA
<213> ORGANISM: Artificial
<220> FEATURE:
<223> OTHER INFORMATION: Synthetic oligonucleotide

<400> SEQUENCE: 9
ggcgccgact ccctgggccg cgaggtgcgc aaccctgcg cctgcttccg caactacgtg       60
cccgtgtgcg gtacc                                                       75

<210> SEQ ID NO 10
<211> LENGTH: 105
<212> TYPE: DNA
<213> ORGANISM: Artificial
<220> FEATURE:
<223> OTHER INFORMATION: Synthetic oligonucleotide

<400> SEQUENCE: 10
ggtaccgacg gcaacaccta ccccaacgag tgcgtgctgt gcttcgagaa ccgcaagcgc      60
cagacctcca tcctgatcca gaagtccggc ccctgctgag gatcc                     105

<210> SEQ ID NO 11
<211> LENGTH: 108
<212> TYPE: DNA
<213> ORGANISM: Artificial
```

```
<220> FEATURE:
<223> OTHER INFORMATION: Synthetic oligonucleotide

<400> SEQUENCE: 11
ggtaccgacg gcaacaccta cggcaacgag tgcatgctga actgcgccga gaaccgcaag    60
cgccagacct ccatcctgat ccagaaggag ggcccctgct gaggatcc               108

<210> SEQ ID NO 12
<211> LENGTH: 25
<212> TYPE: DNA
<213> ORGANISM: Artificial
<220> FEATURE:
<223> OTHER INFORMATION: Synthetic oligonucleotide

<400> SEQUENCE: 12
cgagtgcatg ctgtgcgccg agaac                                          25

<210> SEQ ID NO 13
<211> LENGTH: 25
<212> TYPE: DNA
<213> ORGANISM: Artificial
<220> FEATURE:
<223> OTHER INFORMATION: Synthetic oligonucleotide

<400> SEQUENCE: 13
gttctcggcg cacagcatgc actcg                                          25

<210> SEQ ID NO 14
<211> LENGTH: 107
<212> TYPE: DNA
<213> ORGANISM: Artificial
<220> FEATURE:
<223> OTHER INFORMATION: Synthetic oligonucleotide

<400> SEQUENCE: 14
agatctgacg gaaagaccta cggcaacccc tgcatgctga actgtgccgc ccagaccaag    60
gtgcccgggc tcaagctggt gcacgagggc cgctgctagg cggccgc                 107

<210> SEQ ID NO 15
<211> LENGTH: 37
<212> TYPE: DNA
<213> ORGANISM: Artificial
<220> FEATURE:
<223> OTHER INFORMATION: Synthetic oligonucleotide

<400> SEQUENCE: 15
gctgccttag gcttaggagg atccagcgct gtgaagg                             37

<210> SEQ ID NO 16
<211> LENGTH: 37
<212> TYPE: DNA
<213> ORGANISM: Artificial
<220> FEATURE:
<223> OTHER INFORMATION: Synthetic oligonucleotide

<400> SEQUENCE: 16
ccttcacagc gctggatcct cctaagccta aggcagc                             37

<210> SEQ ID NO 17
<211> LENGTH: 29
<212> TYPE: DNA
<213> ORGANISM: Artificial
<220> FEATURE:
<223> OTHER INFORMATION: Synthetic oligonucleotide
```

-continued

```
<400> SEQUENCE: 17
cgcgcggccg cgatcctcag caggggccg                                           29

<210> SEQ ID NO 18
<211> LENGTH: 42
<212> TYPE: DNA
<213> ORGANISM: Artificial
<220> FEATURE:
<223> OTHER INFORMATION: Synthetic oligonucleotide

<400> SEQUENCE: 18
gcgggatccg gggggagcgg cggctccgac tccctgggcc gc                            42

<210> SEQ ID NO 19
<211> LENGTH: 18
<212> TYPE: DNA
<213> ORGANISM: Artificial
<220> FEATURE:
<223> OTHER INFORMATION: Synthetic oligonucleotide

<400> SEQUENCE: 19
ctgctggcgg ccgcctag                                                       18

<210> SEQ ID NO 20
<211> LENGTH: 650
<212> TYPE: PRT
<213> ORGANISM: Homo sapiens

<400> SEQUENCE: 20
```

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

-continued

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Ser Gly
            580                 585                 590

Gly Ser Asp Ser Leu Gly Arg Glu Ala Lys Cys Tyr Asn Glu Leu Asn
        595                 600                 605

Gly Cys Thr Lys Ile Tyr Asp Pro Val Cys Gly Thr Asp Gly Asn Thr
    610                 615                 620

Tyr Pro Asn Glu Cys Val Leu Cys Phe Glu Asn Arg Lys Arg Gln Thr
625                 630                 635                 640

Ser Ile Leu Ile Gln Lys Ser Gly Pro Cys
                645                 650
```

-continued

<210> SEQ ID NO 21
<211> LENGTH: 647
<212> TYPE: PRT
<213> ORGANISM: Homo sapiens

<400> SEQUENCE: 21

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

```
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Ser Gly
            580                 585                 590

Gly Ser Asp Ser Leu Gly Arg Glu Val Arg Asn Pro Cys Ala Cys Phe
        595                 600                 605

Arg Asn Tyr Val Pro Val Cys Gly Thr Asp Gly Asn Thr Tyr Pro Asn
    610                 615                 620

Glu Cys Val Leu Cys Phe Glu Asn Arg Lys Arg Gln Thr Ser Ile Leu
625                 630                 635                 640

Ile Gln Lys Ser Gly Pro Cys
                645

<210> SEQ ID NO 22
<211> LENGTH: 647
<212> TYPE: PRT
<213> ORGANISM: Homo sapiens

<400> SEQUENCE: 22

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

```
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
```

```
Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
            565                 570                 575

Ala Ala Ser Gln Ala Ala Leu Gly Leu Gly Ser Gly Gly Ser Gly
            580                 585                 590

Gly Ser Asp Ser Leu Gly Arg Glu Val Arg Asn Pro Cys Ala Cys Phe
            595                 600                 605

Arg Asn Tyr Val Pro Val Cys Gly Thr Asp Gly Asn Thr Tyr Gly Asn
            610                 615                 620

Glu Cys Met Leu Cys Ala Glu Asn Arg Lys Arg Gln Thr Ser Ile Leu
625                 630                 635                 640

Ile Gln Lys Glu Gly Pro Cys
                645

<210> SEQ ID NO 23
<211> LENGTH: 648
<212> TYPE: PRT
<213> ORGANISM: Homo sapiens

<400> SEQUENCE: 23

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
    115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu Gly Gly Ser Gly Ser Gly
            580                 585                 590

Gly Ser Asp Ser Leu Gly Arg Glu Val Arg Asn Pro Cys Ala Cys Phe
            595                 600                 605

Arg Asn Tyr Val Pro Val Cys Gly Thr Asp Gly Asn Thr Tyr Gly Asn
            610                 615                 620

Glu Cys Met Leu Asn Cys Ala Glu Asn Arg Lys Arg Gln Thr Ser Ile
625                 630                 635                 640

Leu Ile Gln Lys Glu Gly Pro Cys
                645

<210> SEQ ID NO 24
<211> LENGTH: 647
<212> TYPE: PRT
<213> ORGANISM: Homo sapiens -continued

```
<400> SEQUENCE: 24

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415
```

```
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Ser Gly Gly Ser Gly
            580                 585                 590

Gly Ser Asp Ser Leu Gly Arg Glu Val Arg Asn Pro Cys Ala Cys Phe
            595                 600                 605

Arg Asn Tyr Val Pro Val Cys Gly Ser Asp Gly Lys Thr Tyr Gly Asn
            610                 615                 620

Pro Cys Met Leu Asn Cys Ala Ala Gln Thr Lys Val Pro Gly Leu Lys
625                 630                 635                 640

Leu Val His Glu Gly Arg Cys
                645

<210> SEQ ID NO 25
<211> LENGTH: 294
<212> TYPE: PRT
<213> ORGANISM: Homo sapiens

<400> SEQUENCE: 25

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Cys Ala Glu Asn Arg Lys Arg Gln Thr Ser Ile Leu Ile Gln
        35                  40                  45

Lys Glu Gly Pro Cys Gly Gly Ser Gly Gly Ser Gly Gly Ser Glu Pro
    50                  55                  60

Lys Ser Cys Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Arg Glu Glu Gln Tyr Asn
    130                 135                 140
```

```
Ser Thr Tyr Arg Val Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 26
<211> LENGTH: 48
<212> TYPE: PRT
<213> ORGANISM: Homo sapiens

<400> SEQUENCE: 26

Glu Gly Gly Glu Pro Cys Ala Cys Pro His Ala Leu His Arg Val Cys
1               5                   10                  15

Gly Ser Asp Gly Glu Thr Tyr Ser Asn Pro Cys Thr Leu Asn Cys Ala
                20                  25                  30

Lys Phe Asn Gly Lys Pro Glu Leu Val Lys Val His Asp Gly Pro Cys
            35                  40                  45
```